United States Patent
Harris et al.

(10) Patent No.: US 6,815,439 B2
(45) Date of Patent: Nov. 9, 2004

(54) SUBSTITUTED AZA-OXINDOLE DERIVATIVES

(75) Inventors: Philip Anthony Harris, Durham, NC (US); Lee Frederick Kuyper, Durham, NC (US); Karen Elizabeth Lackey, Durham, NC (US); James Marvin Veal, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/669,400

(22) Filed: Sep. 23, 2003

(65) Prior Publication Data

US 2004/0072836 A1 Apr. 15, 2004

Related U.S. Application Data

(63) Continuation of application No. 09/914,393, filed as application No. PCT/US00/05583 on Mar. 3, 2000, now Pat. No. 6,624,171.

(30) Foreign Application Priority Data

Mar. 4, 1999 (GB) .............................................. 9904995

(51) Int. Cl.⁷ ...................... A61K 31/33; A61K 31/407; A61K 31/38; C07D 221/00; C07D 471/00
(52) U.S. Cl. .................... 514/183; 514/229.2; 514/299; 514/418; 514/412; 514/430; 546/112; 546/113; 548/452; 548/453; 548/465
(58) Field of Search ................................ 514/183, 418, 514/229.2, 299, 430; 548/452, 453, 465; 546/112, 113; 544/98, 111, 359, 368

(56) References Cited

U.S. PATENT DOCUMENTS

| | | |
|---|---|---|
| 5,051,417 A | 9/1991 | Nadler et al. |
| 5,057,538 A | 10/1991 | Shiraishi et al. |
| 5,089,516 A | 2/1992 | Shiraishi et al. |
| 5,124,342 A | 6/1992 | Kerdesky et al. |
| 5,202,341 A | 4/1993 | Shiraishi et al. |
| 5,374,652 A | 12/1994 | Buzzetti et al. |
| 5,441,880 A | 8/1995 | Beach et al. |
| 5,443,962 A | 8/1995 | Draetta et al. |
| 5,449,755 A | 9/1995 | Roberts et al. |
| 5,488,057 A | 1/1996 | Buzzetti et al. |
| 5,627,207 A | 5/1997 | Buzzetti et al. |
| 5,672,508 A | 9/1997 | Gyruis et al. |
| 5,756,335 A | 5/1998 | Beach et al. |
| 5,770,423 A | 6/1998 | Beach et al. |
| 6,043,254 A | 3/2000 | Grell et al. |

FOREIGN PATENT DOCUMENTS

| | | |
|---|---|---|
| DE | 198 15 020 | 10/1999 |
| DE | 198 16 624 | 10/1999 |
| EP | 0436333 A2 | 7/1991 |
| EP | 0503349 A1 | 9/1992 |
| EP | 0503349 B1 | 1/1995 |
| EP | 0788890 A1 | 8/1997 |
| EP | 19844003 A1 | 3/2000 |
| WO | 93/01182 | 1/1993 |
| WO | 93/10242 | 5/1993 |
| WO | 93/24514 | 12/1993 |
| WO | 94/23029 | 10/1994 |
| WO | 94/28914 | 12/1994 |
| WO | 95/01349 | 1/1995 |
| WO | 96/00226 | 1/1996 |
| WO | 96/16964 | 6/1996 |
| WO | 96/22976 | 8/1996 |
| WO | 96/32380 | 10/1996 |
| WO | 98/50356 | 11/1996 |
| WO | WO 94/40116 | 12/1996 |
| WO | 97/25986 | 1/1997 |
| WO | 97/36867 | 10/1997 |
| WO | 98/05335 | 2/1998 |
| WO | 98/07695 | 2/1998 |
| WO | 98/07835 | 2/1998 |
| WO | 9850356 | * 11/1998 |
| WO | 99/15500 | 4/1999 |
| WO | 99/52869 | 10/1999 |
| WO | 99/62503 | 12/1999 |
| WO | 99/62882 | 12/1999 |

OTHER PUBLICATIONS

H. J. Kallmayer, "Substituierte Isatin–phenylimina," Arch. Pharm. (Weinheim, Ger.). vol. 308, 1975, pp. 742–748.

Mohammed Kamel, et al., "Monoazo Metal Complex Forming Dyes Part V Dyes Derived from Isatin," J. Chem. U.A.R. 9, No. 2, 1996, pp. 139–144.

Vishnu J. Ram, et al., "Pesticidal Mannich Bases Derived from Isatinimines," J. Heterocycle Chem. vol. 23, Sep.–Oct. 1986, pp. 1367–1369.

Xiaoyun Wu, et al., "Chemical Consitutents of Isatis Indigotica," Planta Medica, 1997, pp. 55–57.

Hoessel et al., "Indirubin, the Active Constituent of a Chinese Antileukaemia Medicine, Inhibits Cyclin–Dependent Kinases," Nat. Cell Biol., 1996, pp. 60–67.

H.J. Kallmayer, "Substituiere Isatin–phenylimino," Arch. Pharm., vol. 308, 1975, pp. 742–748.

R.M. Mandelkow et al., FEBS Lett., vol. 314, 1992, p. 315.

A. Sengupta et al., Mol. Cell. Biochem. vol. 167, 1997, p. 99.

K. Yashpal, J. Neurosci., vol. 15, 1995, pp. 3263–3272.

Badger, J. Pharm. Exp. Ther., vol. 279, 1996, p. 1453.

Dvir et al., J. Cell Biol., vol. 113, 1991, p. 857.

(List continued on next page.)

Primary Examiner—Richard L. Raymond
Assistant Examiner—Sudhaker B. Patel
(74) Attorney, Agent, or Firm—John L. Lemanowicz

(57) ABSTRACT

Substituted aza-oxindole derivatives useful as cyclin dependent kinase II inhibitors, for preventing/reducing the severity of epithelial cytotoxicity side-effects (e.g., alopecia, plantar-palmar syndrome, mucositis) induced by chemoptherapy and/or radiation therapy in a patient receiving such therapy.

23 Claims, No Drawings

OTHER PUBLICATIONS

Tanaka et al., Nature, vol. 383, 1996, p. 528.
Hunter and Pines, Cell, vol. 79, 1994, p. 573.
Haijar and Pomerantz, FASEB J., vol. 6, 1992, p. 2933.
Salari, FEBS, vol. 263, 1990, p. 104.
A.C. Borthwick et al., Biochem. Biophys. Res. Commun., vol. 210, 1995, p. 738.
Strawn et al., Cancer Res., vol. 56, 1996, p. 3540.
Jackson et al., J. Pharm. Exp. Ther., vol. 284, 1998, p. 687.
Buchdunger et al., Proc. Nat. Acad. Sci, USA, vol. 952, 1991, p. 2258.
Bolen and Brugge, Ann. Rev. Immunol., vol. 15, 1997, p. 371.
E. Littler, Nature, vol. 358, 1992, p. 160.
Schlesinger and Ullrich, Neuron, 1992, vol. 9, p. 383.

* cited by examiner

SUBSTITUTED AZA-OXINDOLE DERIVATIVES

This application is a continuation of Ser. No. 09/914,393 filed Aug. 28, 2001 now U.S. Pat. No. 6,624,171 which is a national phase filing of PCT/US00/05583 filed Mar. 3, 2000 which claims priority from GB 9904995.9 filed Mar. 4, 1999.

The present invention provides novel compounds, novel compositions and methods for their use and manufacture. The compounds and compositions of the present invention are generally useful pharmacologically as therapeutic agents in disease states alleviated by the inhibition or antagonism of protein kinase activated signalling pathways in general, and in particular in the pathological processes which involve aberrant cellular proliferation, such disease states including tumor growth, restenosis, atherosclerosis, and thrombosis. In particular, the present invention relates to a series of substituted aza-oxindole compounds, which exhibit protein tyrosine kinase and protein serine/threonine kinase inhibition, and which are useful for the prevention of chemotherapy-induced alopecia.

BACKGROUND OF THE INVENTION

Protein kinases play a critical role in the control of cell growth and differentiation and are key mediators of cellular signals leading to the production of growth factors and cytokines. See, for example, Schlessinger and Ullrich, *Neuron* 1992, 9, 383. A partial, non-limiting, list of such kinases includes abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-met, cRaf1, CSF1R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK4, Fps, Frk, Fyn, GSK, gsk3a, gsk3b, Hck, IGF-1R, IKK, IKK1, IKK2, IKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKCα, PKCβ, PKCδ, PKCε, PKCγ, PKCλ, PKCμ, PKCζ, PLK1, Polo-like kinase, PYK2, tie$_1$, tie$_2$, TrkA, TrkB, TrkC, UL13, UL97, VEGF-R1, VEGF-R2, Yes and Zap70. Protein kinases have been implicated as targets in central nervous system disorders such as Alzheimer's (Mandelkow, E. M. et al. *FEBS Lett.* 1992, 314, 315; Sengupta, A. et al. *Mol. Cell. Biochem.* 1997, 167,99), pain sensation (Yashpal, K. *J. Neurosci.* 1995, 15, 3263–72), inflammatory disorders such as arthritis (Badger, *J. Pharm. Exp. Ther.* 1996, 279, 1453), psoriasis (Dvir, et al, *J. Cell Biol.* 1991, 113, 857), bone diseases such as osteoporosis (Tanaka et al, *Nature*, 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al *Cancer Res.* 1996, 56, 3540; Jackson et al *J. Pharm. Exp. Ther.* 1998, 284, 687), restenosis (Buchdunger et al, *Proc, Nat. Acad. Sci USA* 1991, 92, 2258), autoimmune diseases and transplant rejection (Bolen and Brugge, *Ann. Rev. Immunol.* 1997, 15, 371) and infectious diseases such as viral (Littler, E.*Nature* 1992, 358, 160), and fungal infections (Lum, R. T. PCT Int. Appl., WO 9805335 A1 980212).

The signals mediated by kinases have also been shown to control growth, death and differentiation in the cell by regulating the processes of the cell cycle (Massague and Roberts, Current Opinion in Cell Biology 1995, 7, 769–72). Progression through the eukaryotic cell cycle is controlled by a family of kinases called cyclin dependent kinases (CDKs) (Myerson, et al., EMBO Journal 1992, 11, 2909). The coordinate activation and inactivation of different cyclin/CDK complexes is necessary for normal progression through the cell cycle (Pines, Trends in Biochemical Sciences 1993, 18, 195; Sherr, Cell 1993, 73, 1059). Both the critical G1-S and G2-M transitions are controlled by the activation of different cyclin/CDK activities. In G1, both cyclin D/CDK4 and cyclin E/CDK2 are thought to mediate the onset of S-phase (Matsushime, et al., Molecular & Cellular Biology 1994, 14, 2066; Ohtsubo and Roberts, Science 1993, 259, 1908; Quelle, et al., Genes & Development 1993, 7, 1559; Resnitzky, et al., Molecular & Cellular Biology 1994, 14, 1669). Progression through S-phase requires the activity of cyclin A/CDK2 (Girard, et al., Cell 1991, 67, 1169; Pagano, et al., EMBO Journal 1992, 11, 961; Rosenblatt, et al., Proceedings of the National Academy of Science USA 1992, 89, 2824; Walker and Maller, Nature 1991, 354, 314; Zindy, et al., Biochemical & Biophysical Research Communications 1992, 182, 1144) whereas the activation of cyclin A/cdc2 (CDK1) and cyclin B/cdc2 are required for the onset of metaphase (Draetta, Trends in Cell Biology 1993, 3, 287; Murray and Kirschner, Nature 1989, 339, 275; Solomon, et al., Molecular Biology of the Cell. 1992, 3, 13; Girard, et al., Cell 1991, 67, 1169; Pagano, et al., EMBO Journal 1992, 11, 961; Rosenblatt, et al., Proceedings of the National Academy of Science USA 1992, 89, 2824; Walker and Maller, Nature 1991, 354, 314; Zindy, et al., Biochemical & Biophysical Research Communications 1992, 182, 1144). It is not surprising, therefore, that the loss of control of CDK regulation is a frequent event in hyperproliferative diseases and cancer (Pines, Current Opinion in Cell Biology 1992, 4, 144; Lees, Current Opinion in Cell Biology 1995, 7, 773; Hunter and Pines, Cell 1994, 79, 573). The selective inhibition of CDKs is therefore an object of the present invention.

SUMMARY OF THE INVENTION

In brief summary, the invention comprises compounds of the formula (I):

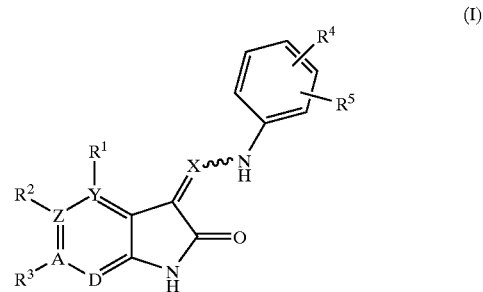

wherein X is selected from the group consisting of: N, CH, CCF$_3$, and C(C$_{1-12}$ aliphatic);

Y is C or N, with the proviso that when Y is N, R$^1$ is absent, and Z, A and D are each C;

Z is C or N, with the proviso that when Z is N, R$^2$ is absent, and Y, A and D are each C;

A is C or N, with the proviso that when A is N, R$^3$ is absent, and Y, Z and D are each C;

D is C or N, with the proviso that when D is N, then Y, Z and A are each C; with the further proviso that Y, Z, A and D do not simultaneously all represent C;

R$^1$ is selected from the group consisting of: hydrogen, C$_{1-12}$ aliphatic, thiol, hydroxy, hydroxy-C$_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide and nitro, where $R^6$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl and $C_{1-12}$ aliphatic-aminosulfonyl, where $R^6$ Aryl and Het are as defined below;

$R^1$ and $R^2$ are optionally joined to form a fused ring selected from the group as defined for Het below, and said fused ring is optionally substituted by one or more substituents selected from the group consisting of: $C_{1-12}$ aliphatic, halogen, nitro, cyano, $C_{1-12}$ alkoxy, carbonyl-$C_{1-12}$ alkoxy and oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy and halogen, where Aryl and Het are as defined below;

$R^2$ and $R^3$ are optionally joined to form a fused ring selected from the group as defined for Het below, and said fused ring is optionally substituted by $C_{1-6}$ aliphatic and/or $C_{1-6}$ aliphatic-carbonyl;

$R^4$ is selected from the group consisting of: sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino, Het-amino, Het-sulfonyl, Het-aminosulfonyl, aminoiminoamino and aminoiminoaminosulfonyl, where $R^7$, $R^8$, Aryl and Het are as defined below;

$R^5$ is hydrogen or $R^4$ and $R^5$ are optionally joined to form a fused ring selected from the group as defined for Het below, and said fused ring is optionally substituted by one or more substituents selected from the group consisting of: $C_{1-12}$ aliphatic, oxo and dioxo;

$R^6$ is selected from the group consisting of: $C_{1-12}$ aliphatic, hydroxy, $C_{1-12}$ alkoxy and halogen;

$R^7$ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxy-alkoxyalkoxyaliphatic and hydroxyl, where Het and Aryl are as defined below;

$R^8$ is selected from the group consisting of: hydrogen, nitro, cyano, $C_{1-12}$ alkoxy, halo, carbonyl-$C_{1-12}$ alkoxy and halo-$C_{1-12}$ aliphatic;

Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, quinoline, tetrahydrofuran, tetrazine, thidiazine, thiadiazole, thiatriazole, thiazine, thiazole, thiomorpholine, thiophene, thiopyran, triazine and triazole;

and the salts, esters, amides, carbamats, solvates, polymorphs, hydrates, polymorphs, affinity reagents and/or prodrugs thereof, in either crystalline or amorphous form.

The esters, amides and and carbamates are preferably hydrolyzable and are more preferably biohydrolyzable. The salts are preferably pharmaceutically acceptable salts.

A more preferred genus of compounds. of the present invention includes compounds of formula (I), defined as follows:

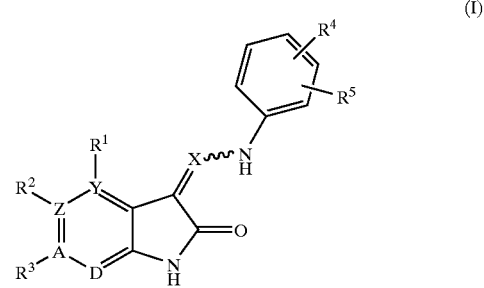

(I)

wherein X is selected from the group consisting of: N, CH and C($C_{1-6}$ aliphatic);

Y is C or N, with the proviso that when Y is N, $R^1$ is absent, and Z, A and D are each C;

Z is C or N, with the proviso that when Z is N, $R^2$ is absent, and Y, A and D are each C;

A is C or N, with the proviso that when A is N, $R^3$ is absent, and Y, Z and D are each C;

D is C or N, with the proviso that when D is N, then Y, Z and A are C;

with the further proviso that Y, Z, A and D do not simultaneously all represent C;

$R^1$ is selected from the group consisting of: hydrogen, $C_{1-6}$ aliphatic, hydroxy-$C_{1-6}$ aliphatic, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, di-$C_{1-6}$ aliphatic amino, di-$C_{1-6}$ aliphatic aminocarbonyl, di-$C_{1-6}$ aliphatic aminosulfonyl, $C_{1-6}$ alkoxycarbonyl, halogen and nitro, where $R^6$, Aryl, Cyc and Het are as defined below;

$R^2$ is selected from the group consisting of: hydrogen, $C_{1-6}$ aliphatic, $R^7$-$C_{1-6}$ aliphatic, $C_{1-6}$ alkoxy, hydroxy-$C_{1-6}$ aliphatic, $C_{1-6}$ alkoxycarbonyl, carboxyl $C_{1-6}$ aliphatic, Aryl, $R^6$-Aryl-oxycarbonyl, $R^6$-oxycarbonyl-Aryl, Het, aminocarbonyl, $C_{1-6}$ aliphatic-aminocarbonyl, Aryl-$C_{1-6}$ aliphatic-aminocarbonyl, $R^6$-Aryl-$C_{1-6}$ aliphatic-aminocarbonyl, Het-$C_{1-6}$ aliphatic-aminocarbonyl, hydroxy-$C_{1-6}$ aliphatic-aminocarbonyl, $C_{1-6}$-alkoxy-$C_{1-6}$ aliphatic-aminocarbonyl, $C_{1-6}$ alkoxy-$C_{1-6}$ aliphatic-amino, di-$C_{1-6}$ aliphatic amino, di-$C_{1-6}$ aliphatic aminocarbonyl, di-$C_{1-6}$ aliphatic aminosulfonyl, halogen, hydroxy, nitro, sulfo, $C_{1-6}$ aliphatic-sulfonyl, aminosulfonyl, $C_{1-6}$ aliphatic-aminosulfonyl and quaternary ammonium, where $R^6$, $R^7$, Aryl and Het are as defined below;

$R^1$ and $R^2$ are optionally joined to form a fused ring selected from the group as defined for Het below, and said fused ring is optionally substituted by halogen and/or oxo;

$R^3$ is selected from the group consisting of: hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl, $C_{1-6}$ alkoxy, Aryl, Aryloxy, hydroxy-Aryl, Het, hydroxy-Het, Het-oxy and halogen, where Aryl and Het are as defined below;

$R^2$ and $R^3$ are optionally joined to form a fused select d from the group as defined for Het below, and said fused ring is optionally substituted by $C_{1-6}$ aliphatic or $C_{1-6}$ aliphatic-carbonyl;

$R^4$ is selected from the group consisting of: sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino Het-amino, Het-sulfonyl, Het-aminosulfonyl aminoiminoamino and aminoiminoaminosulfonyl, where $R^7$, $R^8$, Aryl and Het are as defined below;

$R^5$ is hydrogen;

$R^4$ and $R^5$ are optionally joined to form a fused ring selected from the group as defined for Het below, and said fused ring is optionally substituted by oxo or dioxo;

$R^6$ is selected from the group consisting of: hydrogen, $C_{1-6}$ aliphatic, hydroxy, $C_{1-6}$ alkoxy and halogen;

$R^7$ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxy-alkoxyalkoxyaliphatic and hydroxyl, where Het and Aryl are as defined below;

$R^8$ is hydrogen and/or halo-$C_{1-6}$ aliphatic;

Aryl is phenyl or naphthyl;

Cyc is selected from th group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole; and the salts, esters, amides, carbamates, solvates, polymorphs, hydrates, affinity reagents and/or prodrugs thereof, in either crystalline or amorphous form. The esters, amides and carbamates are preferably hydrolyzable and are more preferably biohydryzeable. The salts are preferably pharmaceutically acceptable salts.

A highly preferred genus of compounds of the present invention includes compounds of formula (I), defined as follows:

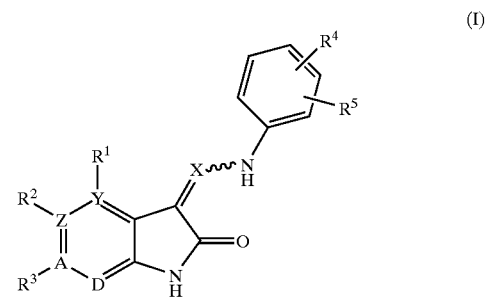

(I)

wherein X is selected from the group consisting of: N, CH and $CCH_3$;

Y is C or N, with the proviso that when Y is N, $R^1$ is absent, and Z, A and D are each C;

Z is C or N, with the proviso that when Z is N, $R^2$ is absent, and Y, A and D are each C;

A is C or N, with the proviso that when A is N, $R^3$ is absent, and X, Y and D are each C;

D is C or N, with the proviso that when D is N, then Y, Z and A are each C; with the further proviso that Y, Z, A and D do not simultaneously all represent C;

$R^1$ is selected from the group consisting of: hydrogen, $C_{,1}$ aliphatic; hydroxy-$C_{1-6}$ aliphatic, di-$C_{1-6}$ aliphatic amino, di-$C_{1-6}$ aliphatic aminocarbonyl, di-$C_{1-6}$ aliphatic aminosulfonyl, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, $C_{1-6}$ alkoxycarbonyl, halogen and nitro, where $R^6$, Aryl, Cyc and Het are as defined below;

$R^2$ is selected from the group consisting of: hydrogen, $C_{1-6}$ aliphatic, N-hydroxyimino-$C_{1-6}$ aliphatic, $C_{1-6}$ alkoxy, $C_{1-6}$ alkoxycarbonyl, Aryl, $R^6$-Aryloxycarbonyl, Het, aminocarbonyl, $C_{1-6}$ aliphatic aminocarbonyl, Aryl-$C_{1-6}$ aliphatic aminocarbonyl, $R^6$-Aryl-$C_{1-6}$ aliphatic aminocarbonyl, Het-$C_{1-6}$ aliphatic aminocarbonyl, di-$C_{1-6}$ aliphatic amino, di-$C_{1-6}$ aliphatic aminocarbonyl, di-$C_{1-6}$ aliphatic aminosulfonyl, hydroxy-$C_{1-6}$ aliphatic aminocarbonyl, $C_{1-6}$-alkoxy-$C_{1-6}$ aliphatic aminocarbonyl, $C_{1-6}$ alkoxy-$C_{1-6}$ aliphatic amino, halogen, hydroxy, nitro, $C_{1-6}$ aliphatic sulfonyl, aminosulfonyl and $C_{1-6}$ aliphatic aminosulfonyl, where $R^6$, Aryl and Het are as defined below;

$R^1$ and $R^2$ are optionally joined to form a fused ring selected from the group as defined for Het below, and said fused ring is optionally substituted by halogen and/or oxo;

$R^3$ is selected from th group consisting of: hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl $C_{1-6}$ alkoxy, Aryloxy, Het and halogen, where Aryl and Het are as defined below;

$R^2$ and $R^3$ are optionally joined to form a fused ring selected from the group as defined for Het below, and said fused ring is optionally substituted by $C_{1-6}$ alkyl and/or $C_{1-6}$ alkylcarbonyl;

$R^4$ is selected from the group consisting of: $R^7$-sulfonyl, $R^7$-sulfonyl $C_{1-6}$-aliphatic, $C_{1-6}$ aliphatic sulfonyl-$C_{1-6}$ aliphatic, $R^7$-aminosulfonyl, di-$C_{1-6}$ aliphatic amino, di-$C_{1-6}$ aliphatic aminocarbonyl, di-$C_{1-6}$ aliphatic aminosulfonyl, di-$C_{1-6}$ aliphatic aminosulfonyl-$C_{1-6}$ aliphatic, $R^7$-aminosulfonyl $C_{1-6}$ aliphatic, aminosulfonylamino, $R^7$-$C_{1-6}$ aliphatic. aminosulfonyl-$C_{1-6}$ aliphatic, Aryl, Het, $R^7$-Aryl-aminosulfonyl, Het-aminosulfonyl and aminoiminoaminosulfonyl, where; $R^7$, $R^8$, Aryl and Het are as defined below;

$R^5$ is hydrogen;

$R^4$ and $R^5$ are optionally joined to form a fused ring selected from the group as defined for Het below, and said used ring is optionally substituted by oxo or dioxo;

$R^6$ is selected from the group consisting of: hydroxy, $C_{1-6}$ alkoxy and halogen;

$R^7$ is selected, from the group consisting of: hydrogen, $C_{1-6}$ aliphatic, hydroxy $C_{1-6}$ alkoxy, hydroxy-$C_{1-6}$ aliphatic, $C_{1-6}$ aliphatic carbonyl, Aryl-carbonyl, $C_{1-12}$ alkoxyalkoxyalkoxyalkoxyalkyl, hydroxyl, Aryl, Aryl-$C_{1-6}$-alkoxy, Aryl-$C_{1-6}$-aliphatic, Het, Het-$C_{1-6}$-alkoxy, di-Het-$C_{1-6}$-alkoxy, Het-$C_{1-6}$-aliphatic and di-Het-$C_{1-6}$ aliphatic;

$R^8$ is trifluoromethyl;

Aryl is phenyl;

Cyc is cyclobutyl;

Het is a saturated or unsaturated heteroatom ring system selected from the group consisting of: benzimidazole, dihydrothiophene, dioxolane, furan, imidazole, morpholine, oxazole, pyridine, pyrrole, pyrrolidine, thiadiazole, thiazole, thiophene, and triazole;

and the salts, esters, amides, carbamates, solvates, polymorphs, hydrates, affinity reagents and/or prodrugs thereof, in either crystalline or amorphous form. The esters, amides and carbamates are preferably hydrolyzable and are more preferably biohydrolyzable. The salts are preferably pharmaceutically acceptable salts.

A preferred group of compounds of the present invention with respect to the substitutions at $R^4$ are compounds of formula (I):

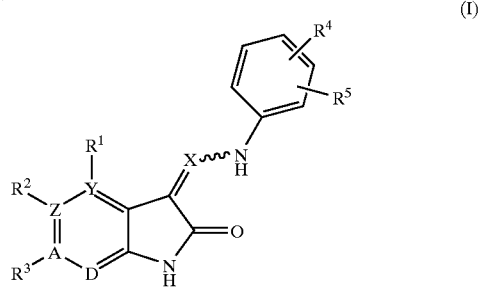

(I)

wherein X is N or CH;

Y is C or N, with the proviso that when Y is N, $R^1$ is absent, and Z, A and D are each C;

Z is C or N, with the proviso that when Z is N, $R^2$ is absent, and Y, A and D are each C;

A is C or N, with the proviso that when A is N, $R^3$ is absent, and Y, Z and D are each C;

D is C or N, with the proviso that when D is N, Y, Z and A are each C;

with th further proviso that Y, Z, A and D do not simultaneously all represent C;

$R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide and nitro, where $R^6$, Aryl, Cyc and Het are as defined below;

$R^2$ is selected from the group consisting of: hydrogen, $C_{1-2}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl and $C_{1-12}$ aliphatic-aminosulfonyl, where $R^6$, Aryl and Het are as defined below;

$R^1$ and $R^2$ are optionally joined to form a fused ring selected from the group as defined for Het below, and said fused ring is optionally substituted by one or more substituents selected from the group consisting of: halogen, nitro, cyano, $C_{1-12}$ alkoxy, carbonyl-$C_{1-12}$ alkoxy and oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

$R^2$ and $R^3$ are optionally joined to form a fused ring select d from the group as defined for Het below, and said fused ring is optionally substituted by $C_{1-6}$ aliphatic and/or $C_{1-6}$ aliphatic-carbonyl;

$R^4$ is selected from the group consisting of: $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic aminosulfonyl, di-$C_{1-12}$ aliphatic aminosulfonyl-$C_{1-12}$ aliphatic, $(R^8)_{1-3}$-Aryl-aminosulfonyl, $(R^8)_{1-3}$-Aryl-sulfonylamino and aminoiminoaminosulfonyl, where $R^7$, $R^8$, Aryl and Het are as defined below;

$R^5$ is hydrogen;

$R^4$ and $R^5$ are optionally joined to form a fused ring selected from the group as defined for Het below, and said fused ring is optionally substituted by oxo or dioxo;

$R^8$ is selected from the group consisting of: $C_{1-12}$ aliphatic, hydroxy, $C_{1-12}$ alkoxy and halogen;

R$^7$ is selected from the group consisting of: hydrogen, C$_{1-12}$ aliphatic, C$_{1-12}$ alkoxy, hydroxy-C$_{1-12}$ alkoxy, hydroxy-C$_{1-12}$ aliphatic, carboxylic acid, C$_{1-12}$ aliphatic-carbonyl, Het, Het-C$_{1-12}$-aliphatic, Het-C$_{1-12}$-alkoxy, di-Het-C$_{1-12}$-alkoxy Aryl, Aryl-C$_{1-12}$-aliphatic, Aryl-C$_{1-12}$-alkoxy, Aryl-carbonyl, C$_{1-18}$ alkoxyalkoxyalkoxyalkoxyaliphatic and hydroxyl, where Het and Aryl are as defined below;

R$^8$ is selected from the group consisting of: hydrogen, nitro, cyano, C$_{1-12}$ alkoxy, halo, carbonyl-C$_{1-12}$ alkoxy and halo-C$_{1-12}$ aliphatic; and Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole;

and the salts, esters, amides, carbamates, solvates, polymorphs, hydrates, affinity reagents and/or prodrugs thereof, in either crystalline or amorphous form. The esters, amides and carbamates are preferably hydrolyzable and are more preferably biohydrolyzeable. The salts are preferably pharmacetically acceptable salts.

A preferred group of compounds of the present invention with respect to the substitutions at R$^4$ are compounds of formula (I):

(I)

wherein X is CH;

Y is C or N, with the proviso that when Y is N, R$^1$ is absent, and Z, A and D are each C;

Z is C or N, with the proviso that when Z is N, R$^2$ is absent, and Y, A and D are each C;

A is C or N, with the proviso that when A is N, R$^3$ is absent, and Y, Z and D are each C;

D is C or N, with the proviso that when D is N, Y, Z and A are each C; with the further proviso that Y, Z, A and D do not simultaneously all represent C;

R$^1$ is hydrogen;

R$^2$ is selected from the group consisting of: hydrogen, C$_{1-12}$ alkoxycarbonyl, Aryl, Het and halogen, where Aryl and Het are as defined below;

R$^3$ is hydrogen or halogen;

R$^4$ is selected from the group consisting of: R$^7$-aminosulfonyl, R$^7$-aminosulfonyl-C$_{1-12}$ aliphatic, R$^7$-sulfonylamino, R$^7$ sulfonylamino-C$_{1-12}$ aliphatic, aminosulfonylamino, di-C$_{1-12}$ aliphatic aminosulfonyl, di-C$_{1-12}$ aliphatic aminosulfonyl-C$_{1-12}$ aliphatic, (R$^8$)$_{1-3}$-Aryl-aminosulfonyl, (R$^8$)$_{1-3}$-Aryl-sulfonylamino and aminoiminoaminosulfonyl, where R$^7$, R$^8$, Aryl and Het are as defined below;

R$^5$ is hydrogen;

R$^4$ and R$^5$ are optionally joined to form a fused ring selected from the group as defined for Het below, and said used ring is optionally substituted by oxo or dioxo;

R$^7$ is selected from the group consisting of: hydrogen, C$_{1-12}$ aliphatic, C$_{1-12}$ alkoxy, hydroxy-C$_{1-12}$ alkoxy, hydroxy-C$_{1-12}$ aliphatic, carboxylic acid, C$_{1-12}$ aliphatic-carbonyl, Het, Het-C$_{1-12}$-aliphatic, Het-C$_{1-12}$-alkoxy, di-Het-C$_{1-12}$-alkoxy Aryl, Aryl-C$_{1-12}$-aliphatic, Aryl-C$_{1-12}$-alkoxy, Aryl-carbonyl, C$_{1-18}$ alkoxyalkoxyalkoxyalkoxyaliphatic and hydroxyl, where Het and Aryl are as defined below;

R$^8$ is selected from the group consisting of: hydrogen, nitro, cyano, C$_{1-12}$ alkoxy, halo, carbonyl-C$_{1-12}$ alkoxy and halo-C$_{1-12}$ aliphatic;

Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl or cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole;

and the salts, esters, amides, carbamates solvates, polymorphs, hydrates, affinity reagents and/or prodrugs thereof, in either crystalline or amorphous form. The esters, amides and carbamates are preferably hydrolyzable and are more preferably biohydrolyzable. The salts are preferably pharmaceutically acceptable salts.

Due to the presence of an oxindole exocyclic double bond, also included in the compounds of the invention are their respective pure E and Z geometric isomers as well as mixtures of E and Z isomers. The invention as described and claimed does not set any limiting ratios on prevalence of Z to E isomers. Thus, for example, compound number 1 in the tables below is disclosed and claimed as the E geometric isomer thereof, the Z geometric isomer thereof, and a mixture of the E and Z geometric isomers thereof, but not limited by any given ratio(s).

Likewise, it is understood that compounds of formula (I) may exist in tautomeric forms other than that shown in the formula.

Certain of the compounds as described will contain one or more chiral, or asymmetric, centers and will therefore be capable of existing as optical isomers that are either dextrorotatory or levorotatory. Also included in the compounds of the invention are the respective dextrorotatory or levorotatory pure preparations, and mixtures thereof.

Certain compounds of formula (I) above may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula, and these are also included within the scope of the present invention.

The present invention also provides compounds of formula (I) and pharmaceutically acceptable salts thereof (hereafter identified as the "active compounds") for use in medical therapy, and particularly in the treatment of disorders mediated by CDK2 activity, such as alopecia induced by cancer chemotherapy.

A further aspect of the invention provides a method of treatment of a human or animal body suffering from a disorder kinase is a mitogen activated protein kinase which comprises administering an effective amount of an active compound of formula (I) to the human,or animal patient.

Another aspect of the present invention, provides the use of an active compound of formula (I), in the preparation of a medicament for the treatment of malignant tumors, or for the treatment of alopecia induced by cancer chemotherapy or induced by radiation therapy. Alternatively, compounds of formula (I) can be used in the preparation of a medicament for the treatment of a disease mediated by a kinase selected from the group consisting of: abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-m t, cRaf1, CSF1R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK-4, Fps, Frk, Fyn, GSK, gsk3a, gsk3b, Hck, IGF-1R, IKK, IKK1, IKK2, IKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKC$\alpha$, PKC$\beta$, PKC$\delta$, PKC$\epsilon$, PKC$\gamma$, PKC$\lambda$, PKC$\mu$, PKC$\zeta$, PLK1, Polo-like kinase, PYK2, tie$_1$, tie$_2$, TrkA, TrkB, TrkC, UL13, UL97, VEGF-R1, VEGF-R2, Yes and Zap70. Additionally, compounds of formula (I) can be used in the preparation of a medicament for the treatment of a disease or disorder such as organ transplant rejection, tumor growth, chemotherapy-induced alopecia, chemotherapy-induced thrombocytopenia, chemotherapy-induced leukopenia, mucocitis, plantar-palmar syndrome, restenosis, atherosclerosis, rheumatoid arthritis, angiogenesis, hepatic cirrhosis, glomerulonephritis, diabetic nephropathy, malignant nephrosclerosis, thrombotic microangiopathy, glomerulopathy, psoriasis, diabetes mellitus, inflammation, neurodegenerative disease, macular degeneration, actinic keratosis and hyperproliferative disorders.

Another aspect of the present invention provides the use of an active compound of formula (I), in coadministration with previously known anti-tumor therapies for more effective treatment of such tumors.

Another aspect of the present invention provides the use of an active compound of formula (I) in the preparation of a medicament for the treatment of viral or eukaryotic infection.

Other aspects of the present invention related to the inhibition of mitogen activated protein kinases are discussed in more detail below.

Compounds we have synthesized as part of the present invention which are currently preferred are listed in Tables 1 and 2 below. Compounds are identified by the numbers shown in the first column; variables below in the rest of the columns are with reference to the generic structure (I). Corresponding IUPAC nomenclature are disclosed in Table 2. Since all substituents at each point of substitution are capable of independent synthesis of each other, the tables are to be read as a matrix in which any combination of substituents is within the scope of the disclosure and claims of the invention.

(I)

| Example | Y | Z | A | D | $R^1$ | $R^2$ | $R^3$ | $R^4$ | $R^5$ | X |
|---|---|---|---|---|---|---|---|---|---|---|
| 1 | C | N | C | C | H | — | H | 4'-SO$_2$NH$_2$ | H | CH |
| 2 | C | C | N | C | H | H | — | 4'-SO$_2$NH$_2$ | H | CH |
| 3 | N | C | C | C | — | H | H | 4'-CH=NN(H)-5' | | CH |
| 4 | N | C | C | C | — | H | H | 4'-N=CH—CH=CH-5' | | CH |
| 5 | C | C | C | N | H | H | H | 4'-SO$_2$NH$_2$ | H | CH |
| 6 | C | C | C | N | H | H | H | 4'-CH=NN(H)-5' | | CH |
| 7 | C | C | C | N | H | H | H | 4'-N=CH—CH=CH-5' | | CH |
| 8 | C | C | C | N | H | phenyl | H | 4'-SO$_2$NH$_2$ | H | CH |
| 9 | C | C | C | N | H | phenyl | H | 4'-CH=NN(H)-5' | | CH |
| 10 | C | C | C | N | H | phenyl | H | 4'-N=CH—CH=CH-5' | | CH |
| 11 | C | C | C | N | H | 2-furanyl | H | 4'-SO$_2$NH$_2$ | H | CH |
| 12 | C | C | C | N | H | 2-furanyl | H | 4'-CH=NN(H)-5' | | CH |
| 13 | C | C | C | N | H | 2-furanyl | H | 4'-N=CH—CH=CH-5' | | CH |
| 14 | C | C | C | N | H | 3-thiophenyl | H | 4'-SO$_2$NH$_2$ | H | CH |
| 15 | C | C | C | N | H | 3-thiophenyl | H | 4'-CH=NN(H)-5' | | CH |
| 16 | C | C | C | N | H | 3-thiophenyl | H | 4'-N=CH—CH=CH-5' | | CH |
| 17 | C | C | C | N | H | Br | H | 4'-SO$_2$NH$_2$ | H | CH |

-continued (I)

| Example | Y | Z | A | D | R¹ | R² | R³ | R⁴ | R⁵ | X |
|---|---|---|---|---|---|---|---|---|---|---|
| 18 | C | C | C | N | H | Br | H | | 4'-CH=NN(H)-5' | CH |
| 19 | C | C | C | N | H | Br | H | 4'-N=CH—CH=CH-5' | | CH |
| 20 | C | C | C | N | H | H | Cl | 4'-SO₂NH₂ | H | CH |
| 21 | C | C | C | N | H | H | Cl | | 4'-CH=NN(H)-5' | CH |
| 22 | C | C | C | N | H | H | Cl | 4'-N=CH—CH=CH-5' | | CH |
| 23 | C | C | C | N | H | carbethoxy | H | 4'-SO₂NH₂ | H | CH |
| 24 | C | C | C | N | H | carbethoxy | H | | 4'-CH=NN(H)-5' | CH |
| 25 | C | C | C | N | H | carbethoxy | H | 4'-N=CH—CH=CH-5' | | CH |

Standard accepted nomenclature corresponding to the Examples set forth in this specification are set forth below. In some cases nomenclature is given for one or more possible isomers.

TABLE 2

| No. | UPAG NAME |
|---|---|
| 1 | 4-{[(2-Oxo-1,2-dihydro-3H-pyrrolo[3,2-c]pyridin-3-ylidene)methyl]amino}benzenesulfonamide |
| 2 | 4-{[(2-Oxo-1,2-dihydro-3H-pyrrolo[2,3-c]pyridin-3-ylidene)methyl]amino}benzenesulfonamide |
| 3 | 3-[(1H-Indazol-6-ylamino)methylidene]-1H-pyrrolo[3,2-b]pyridin-2-one |
| 4 | 3-[(6-Quinolinylamino)methylidene]-1,3-dihydro-2H-pyrrolo[3,2-b]pyridin-2-one |
| 5 | 4-{[(2-Oxo-1,2-dihydro-3H-pyrrolo[2,3-b]pyridin-3-ylidene)methyl]amino}benzenesulfonamide |
| 6 | 3-[(1H-Indazol-6-ylamino)methylidene]-1H-pyrrolo[2,3-b]pyridin-2-one |
| 7 | 3-[(6-Quinolinylamino)methylidene]-1,3-dihydro-2H-pyrrolo[2,3-b]pyridin-2-one |
| 8 | 4-{[(2-Oxo-5-phenyl-1,2-dihydro-3H-pyrrolo[2,3-b]pyridin-3-ylidene)methyl]amino}benzenesulfonamide |
| 9 | 3-[(1H-Indazol-6-ylamino)methylidene]-5-phenyl-1H-pyrrolo[2,3-b]pyridin-2-one |
| 10 | 5-Phenyl-3-[(6-quinolinylamino)methylidene]-1,3-dihydro-2H-pyrrolo[2,3-b]pyridin-2-one |
| 11 | 4-({[5-(2-Furyl)-2-oxo-1,2-dihydro-3H-pyrrolo[2,3-b]pyridin-3-ylidene]methyl}amino)benzenesulfonamide |
| 12 | 5-(2-Furyl)-3-[(1H-indazol-6-ylamino)methylidene]-1H-pyrrolo[2,3-b]pyridin-2-one |
| 13 | 5-(2-Furyl)-3-[(6-quinolinylamino)methylidene]-1,3-dihydro-2H-pyrrolo[2,3-b]pyridin-2-one |
| 14 | 4-({[2-Oxo-5-(3-thienyl)-1,2-dihydro-3H-pyrrolo[2,3-b]pyridin-3-ylidene]methyl}amino)benzenesulfonamide |
| 15 | 3-[(1H-Indazol-6-ylamino)methylidene]-5-(3-thienyl)-1,3-dihydro-2H-pyrrolo[2,3-b]pyridin-2-one |
| 16 | 3-[(6-Quinolinylamino)methylidene]-5-(3-thienyl)-1,3-dihydro-2H-pyrrolo[2,3-b]pyridin-2-one |
| 17 | 4-{[(5-Bromo-2-oxo-1,2-dihydro-3H-pyrrolo[2,3-b]pyridin-3-ylidene)methyl]amino}benzenesulfonamide |
| 18 | 5-Bromo-3-[(1H-indazol-6-ylamino)methylidene]-1,3-dihydro-2H-pyrrolo[2,3-b]pyridin-2-one |
| 19 | 5-Bromo-3-[(6-quinolinylamino)methylidene]-1,3-dihydro-2H-pyrrolo[2,3-b]pyridin-2-one |
| 20 | 4-{[(6-Chloro-2-oxo-1,2-dihydro-3H-pyrrolo[2,3-b]pyridin-3-ylidene)methyl]amino}benzenesulfonamide |
| 21 | 6-Chloro-3-[(1H-indazol-6-ylamino)methylidene]-1,3-dihydro-2H-pyrrolo[2,3-b]pyridin-2-one |

TABLE 2-continued

| No. | UPAG NAME |
|---|---|
| 22 | 6-Chloro-3-[(6-quinolinylamino)methylidene]-1,3-dihydro-2H-pyrrolo[2,3-b]pyridin-2-one |
| 23 | Ethyl 3-{[4-(aminosulfonyl)anilino]methylidene}-2-oxo-1,2-dihydro-3H-pyrrolo[2,3-b]pyridine-5-carboxylate |
| 24 | Ethyl 3-[(1H-indazol-6-ylamino)methylidene]-2-oxo-1,2-dihydro-3H-pyrrolo[2,3-b]pyridine-5-carboxylate |
| 25 | Ethyl 2-oxo-3-[(6-quinolinylamino)methylidene]-2,3-dihydro-1H-pyrrolo[2,3-b]pyridine-5-carboxylate |

The invention discloses 10 different points of substitution on structural formula (I). Each of these points of substitution bears a substituent whose selection and synthesis as part of this invention was independent of all other points of substitution on formula (I). Thus, each point of substitution is now further described individually.

Preferred substitutions at the $R^1$ position include hydrogen, halogen, amide, nitro, lower alkyl, hydroxy, hydroxyalkyl, pyrimidineloweralkyl, loweralkoxycarbonyl, cyclic loweralkyl, hydroxyphenylloweralkyl, phenoxy, alkoxy and pyrazole; and $R^1$ fused with $R^2$ to form a fused ring selected from the group consisting of: thiazole, pyrazole, triazole, halogen-substituted diazole, acyl substituted pyrrole and pyridine. Most preferred substituents at $R^1$ include hydrogen and methyl and $R^1$ fused with $R^2$ for form fused thiazole or fused pyridine. The most highly preferred substitution at the $R^1$ position is hydrogen.

Preferred substitutions at the $R^2$ position include hydrogen, halogen, sulfate, amine, quaternary amine, amide, ester, phenyl, alkoxy, aminosulfonyl, lower alkyl sulfonyl, furanyl lower alkyl amide, pyridinyl lower alkyl amide, alkoxy-substituted phenyl lower alkyl amide, morpholino lower alkyl amide, imidazolyl lower alkyl amide, hydroxy lower alkyl amide, alkoxy lower alkyl amide, lower alkyl amide, lower alkyl sulfonamide, lower alkyl hydroxy substituted amino, nitro, halogen-substituted phenoxycarbonyl and triazole and oxazole rings, or are $R^2$ fused with $R^3$ to form a fused ring selected from the group consisting of: oxazole, pyrrole, and dioxolane, which fused ring is optionally substituted by lower alkyl or lower alkyl carbonyl, and which fused ring is optionally a hetero ring having nitrogen as the heteroatom and forming a quaternary ammonium salt ionically bonded with a halogen atom. Most preferred substituents at $R^2$ include hydrogen, phenyl, 2-furanyl, 3-thiophenyl, bromo and carbethoxy.

Preferred substitutions at $R^3$ include hydrogen, lower alkyl, hydroxy lower alkyl, halogen, phenoxy and alkoxy. Most preferred include hydrogen Hand chloro. Most highly preferred is hydrogen.

Preferred substitutions at $R^4$ include sulfonylamino, sulfonylaminoamino, lower alkyl sulfonylamino, lower alkylsulfonyl lower alkyl, alkoxysulfonylamino, phenylcarbonylsulfonylamino, phenoxysulfonyl, hydroxy lower alkylsulfonylamino, hydroxy lower alkylsulfonylamino lower alkyl, alkyl, phenylsulfonylamino (optionally substituted by halogen-substituted lower alkyl), aminoiminosulfonylamino, alkylsulfonylaminoalkyl, pyridinyl lower alkyl sulfonylamino, benzamideazolesulfonylamino, pyridylsulfonylamino, pyrimidinylsulfonylamino, thiadiazolylsulfonylamino (optionally substituted by lower alkyl), thiazolesulfonylamino, hydroxyalkoxyalkylsulfonylamino and 4'-$SO_2NH[(CH_2)_2O]_4CH_3$, or $R^4$ fused with $R^5$ to form a fused ring selected from the group consisting of imidazole, triazole, cyclic sulfonylamino and thiaphene, where said fused ring is optionally disubstituted on the sulfur heteroatom by oxo. The most preferred substitutions include 2-pyridine sulfonylamino, 4-pyridine sulfonylamino, hydroxy n-butyl sulfonylamino, methylsulfonylaminomethylene, sulfonyldimethylamino, fused 1,2-pyrazole and sulfonylamino. In a most highly preferred embodiment, $R^4$ is sulfonylamino or fused 1,2-pyrazole.

The preferred substitution at $R^5$ is hydrogen.

Preferred substitutions at X include N, CH and CCH$_3$. Most preferred is CH.

The preferred substitution at Y is N or C.
The preferred substitution at Z is N or C.
The preferred substitution at A is N or C.
The preferred substitution at D is N or C.

DETAILED DESCRIPTION OF THE INVENTION

Salts encompassed within the term "pharmaceutically acceptable salts" refer to non-toxic salts of the compounds of this invention which are generally, prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconates, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinat, Tannate, Tartrate, Teoclate, Tosylate, Trifluoroacetate, Triethiodide, Trimethylammonium and Valerate.

Other salts which are not pharmaceutically acceptable may be useful in the preparation of compounds of formula (I) and these form a further aspect of the invention.

Also included within the, scope of the invention are the individual isomers of the compounds represented by formula (I) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "aliphatic" refers to the terms alkyl, alkylene, alkenyl, alkenylene, alkynyl and alkynylene.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally. substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl and isopropyl, and the like.

As used herein, the term "alkylene" refers to a straight or branched chain divalent hydrocarbon radical having from one to ten carbon atoms, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene; ethylene, and the like.

As used herein, the term "alkenyl" refers to a hydrocarbon radical having from two to ten carbons and at least one carbon-carbon double bond, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by, alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to an straight or branched chain divalent hydrocarbon radical having from two to ten carbon atoms and one or more carbon-carbon double bonds, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl; nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl; aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, the term "cycloaliphatic" refers to the terms cycloalkyl, cycloalkylene, cycloalkenyl, cycloalkenylene, cycloalkynyl and cycloalkylnylene.

As used herein, "cycloalkyl" refers to a alicyclic hydrocarbon group with one or more degrees of unsaturation, having from three to twelve carton atoms, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes, by way of example, cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of: lower alkyl; lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heteroatom ring system" is inclusive of heterocyclic, heterocyclyl, heteroaryl and heteroarylene ring systems. Non-limiting examples of such heteroatom ring systems are recited in the Summary of the Invention, above.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more other "heterocyclic" rings or cycloalkyl rings. Examples of "heterocyclylene" rings include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings to form anthracene, phenanthrene, or napthalene ring systems, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is aliphatic.

As used herein, the term "alkylsulfanyl" refers to the group $R_aS$—, where $R_a$ is aliphatic.

As used herein, the term "alkylsulfenyl" refers to the group $R_aS(O)$—, where $R_a$ is aliphatic.

As used herein, the term "alkylsulfonyl" refers to the group $R_aSO_2$—, where $R_a$ is aliphatic.

As used herein, the term "acyl" refers to the group $R_aC(O)$—, where $R_a$ is aliphatic, cycloaliphatic, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is aliphatic.

As used herein, the term "acyloxy" refers to the group $R_aC(O)O$—, where $R_a$ is aliphatic, cycloaliphatic, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" is inclusive of embodiments in which a described condition is present and embodiments in which such described condition is not present, for example, where the term is used with reference to a chemical substituent, it indicates the inclusion of embodiments in which the specified substituent is present as well as embodiments in which the specified substituent is not present.

As used herein, the term "substituted" refers to substitution with the named substituent or substituents, multiple degrees of substitution being allowed.

As used herein, the terms "contain" or "containing" in reference to any of the above-defined alkyl, alkenyl, alkynyl or cycloalkyl substituents, are inclusive of in-line substitutions at any position along such alkyl, alkenyl, alkynyl or cycloalkyl substituents, with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

The compounds of the present invention have the ability to crystallize in more than one form, a characteristic which is known as polymorphism, and such polymorphic forms ("polymorphs") are within the scope of the present invention. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the terms "biohydrolyzable carbonate", "biohydrolyzable ureide" and "biohydrolyzable carbamate" include carbonates, ureides, and carbamates, respectively, of a compound of the general formula (I) which carbonates, ureides, and carbamates, do not completely diminish the biological activity of the parent substance. Such biohydrolyzable carbonates, ureides, and carbamates may confer on the parent compound of the general formula (I) advantageous properties in vivo, such as improved duration of action, onset of action, and the like. Also included are compounds which are relatively biologically inactive but which are converted in vivo by the subject to the biologically active principle. An advantage of such biohydrolyzable forms is that, for example, they facilitate improved oral administration because the carbonates, ureides, and carbamates are more readily absorbed from the gut and are then transformed to a compound of formula (I) in plasma. Many of such biohydrolyzable compounds are known in the art and include, byway of example, lower alkyl carbamates.

As used herein, the term "biohydrolyzable ester" is an ester of a compound of general formula which does not completely diminish the biological activity of the parent substance. Such esters may confer on the parent compound of the general formula (I) advantageous properties in vivo, such as improved duration of action, onset of action, and the like. Also included are esters which are relatively biologically inactive but which are converted in vivo by the subject to the biologically active principle. An advantage of such biohydrolyzable esters is that, for example, they facilitate improved oral administration because they are more readily absorbed from the gut and are then transformed to a compound of formula (I) in plasma. Many biohydrolyzable esters are known in the art and include, by way of example, lower alkyl esters, lower acyloxy-alkyl esters, lower alkoxyacyloxyalkyl esters, alkoxyacyloxy esters, alkyl acylamino alkyl esters and choline esters.

As used herein, the term "biohydrolyzable amide" is an amide of a compound of general formula which does not completely diminish the biological activity of the parent substance. Such amides may confer on the parent compound of the general formula (I) advantageous properties in vivo, such as improved duration of action, onset of action, and the like. Also included are amides which are relatively biologically inactive but which are converted in vivo by the subject to the biologically active principle. An advantage of such biohydrolyzable amides is that, for example, they facilitate improved oral administration because they are more readily absorbed from the gut and are then transformed to a compound of formula (I) in plasma. Many biohydrolyzable amides are known in the art and include, by way of example, lower alkyl amides, α-amino acid amides, alkoxyacyl amides and alkylaminoalkylcarbonyl amides.

As used herein, the term "prodrug" includes biohydrolyzable amides, biohydrolyzable esters and biohydrolyzable carbamates and also encompasses compounds in which the biohydrolyzable functionality in such prodrug is encompassed in the compound of formula (I): for example, a lactam formed by a carboxylic group in $R_1$ and an amine in $R_2$, and compounds which may be oxidized or reduced biologically at a given functional group to yield drug substances of formula (I). Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) which does not affect its in vitro biological activity, allowing the compound to bind to a target, yet such a group binds strongly to a third component allowing (a) characterization of the target as to localization within a cell or other organism component, perhaps by visualization by fluorescence or radiography, or (b) facile separation of the target from an unknown mixture of targets, whether proteinaceous or not proteinaceous. An example of an affinity reagent according to (b) would be biotin either directly attached to (I) or linked with a spacer of one to 50 atoms selected from the group consisting of C, H, O, N, S, or P in any combination. An example of an affinity reagent according to (a) above would be fluorescein, either directly attached to (I) or linked with a spacer of one to 50 atoms selected from the group consisting of C, H, O, N, S, or P in any combination.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

Whenever the terms "aliphatic" or "aryl" or either of their prefixes appear in a name of a substituent (e.g. arylalkoxyaryloxy) they shall be interpreted as including those limitations given above for "aliphatic" and "aryl". Aliphatic or cycloalkyl substituents shall be recognized as being term equivalents to those having one or more degrees of unsaturation. Designated numbers of carbon atoms (e.g. $C_{1-10}$) shall refer independently to the number of carbon atoms in an aliphatic or cyclic aliphatic moiety or to the aliphatic portion of a larger substituent in which the term "aliphatic" appears as a prefix (e.g. "al-").

As used herein, the term "disubstituted amine" or "disubstituted amino-" shall be interpreted to include either one or two substitutions on that particular nitrogen atom.

As used herein, the term "oxo" shall refer to the substituent =O.

As used herein, the term. "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

The compounds of formula (I) are readily synthesized using various synthetic procedures known in the art and are readily prepared according to the following reaction Synthesis Schemes (in which all variables are as defined herein) and examples or modifications thereof using readily available starting materials, reagents and conventional synthesis procedures. In these reactions, it is also possible to make use of variants which are themselves known to those of ordinary skill in this art, but are not mentioned in greater detail.

Synthesis Schemes

Scheme 1.
Preparation of pyrrolo[3,2-b]pyridin-2-ones.

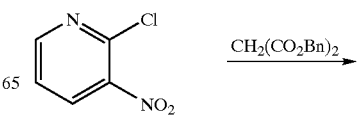

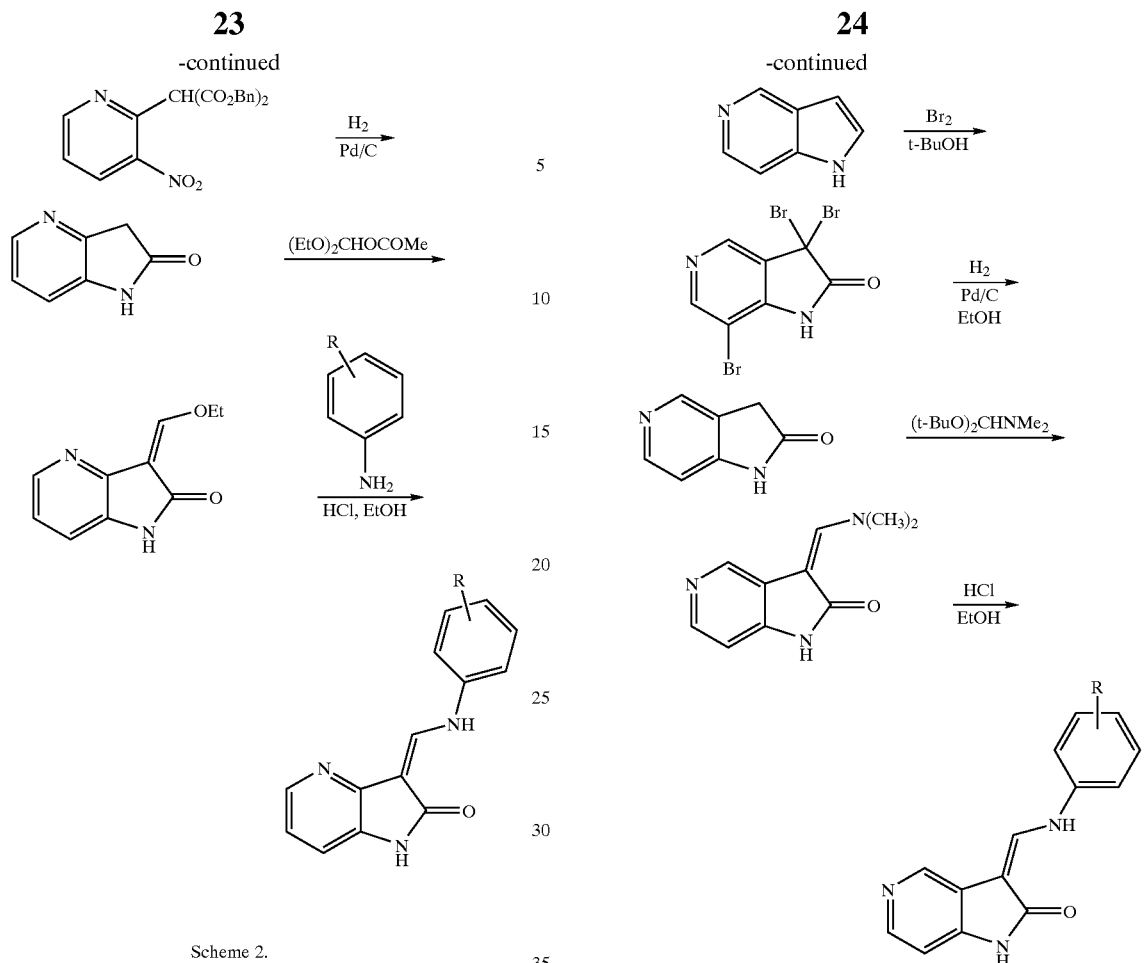
Scheme 2.
Preparation of pyrrolo[3,2-c]pyridin-2-ones.
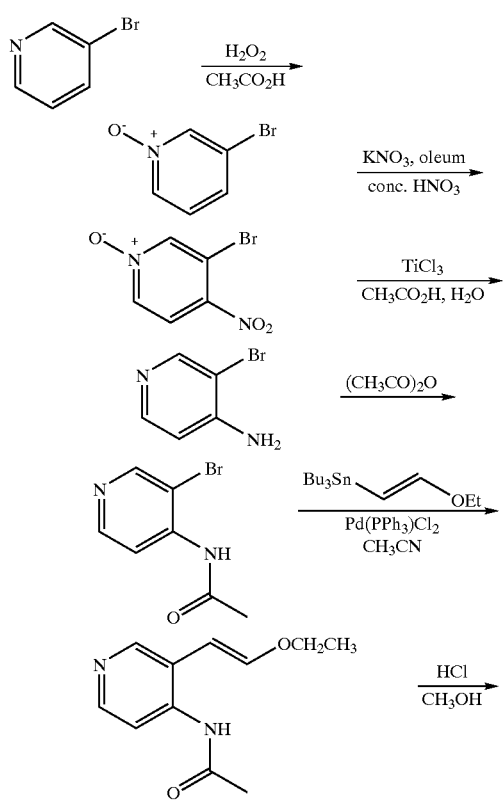
Scheme 3.
Preparation of pyrrolo[2,3-c]pyridin-2-ones.

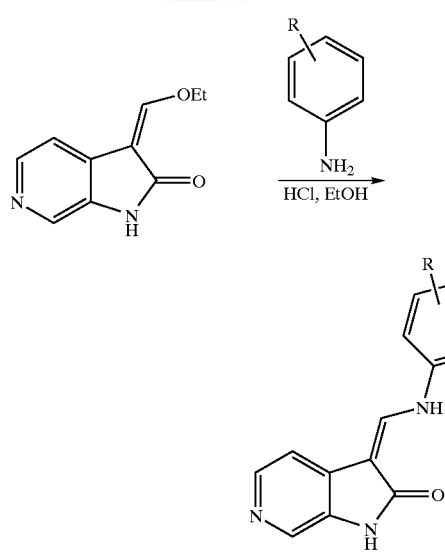
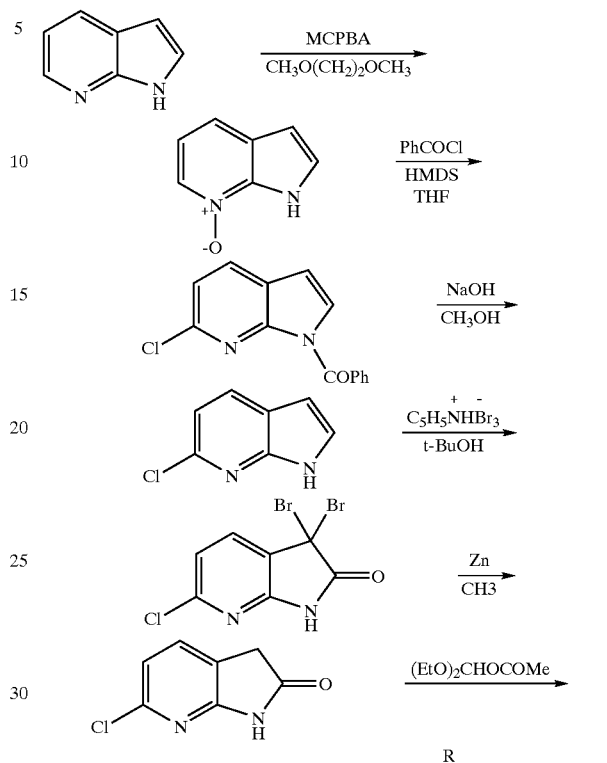
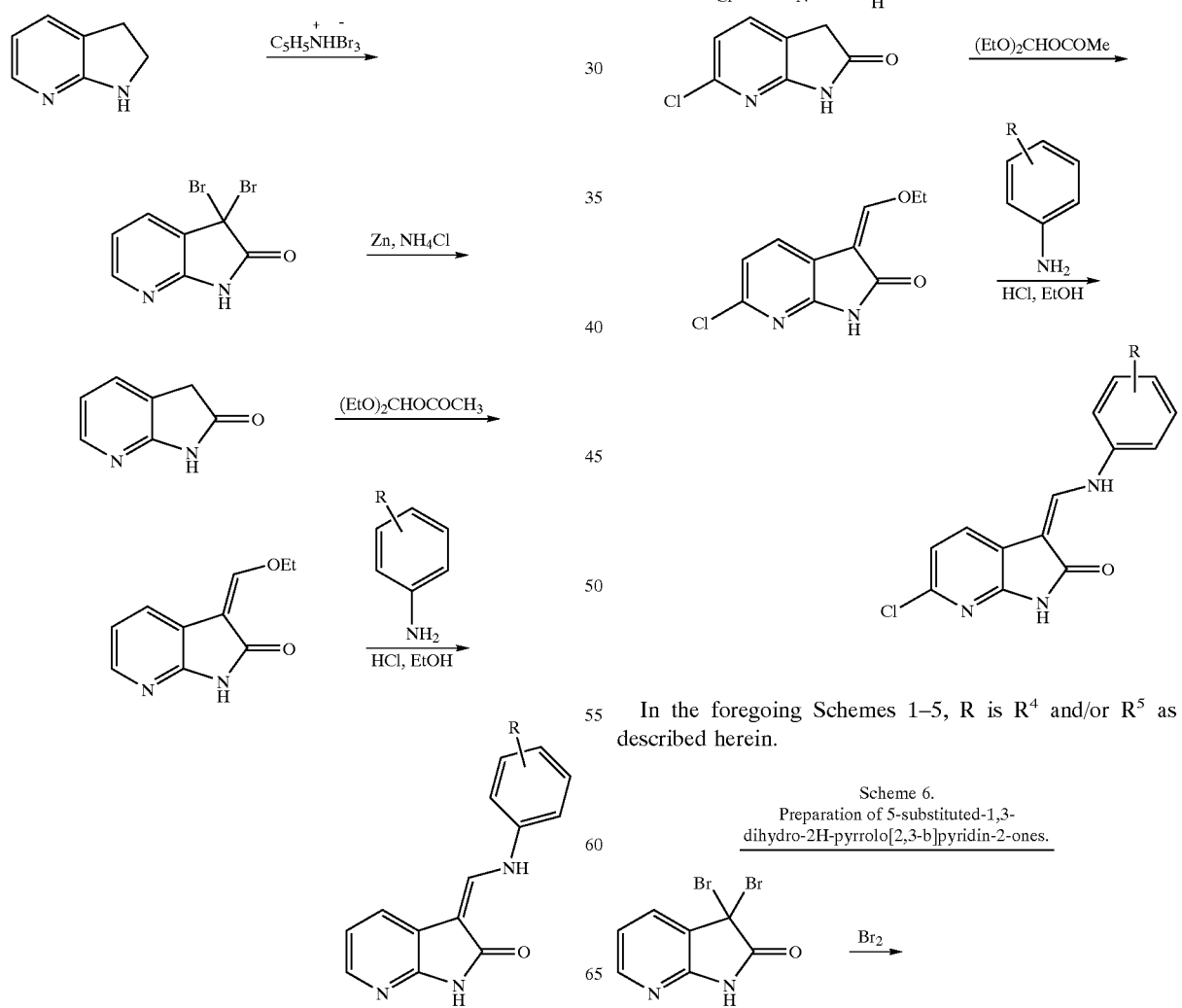
In the foregoing Schemes 1–5, R is $R^4$ and/or $R^5$ as described herein.
Scheme 6.
Preparation of 5-substituted-1,3-dihydro-2H-pyrrolo[2,3-b]pyridin-2-ones.

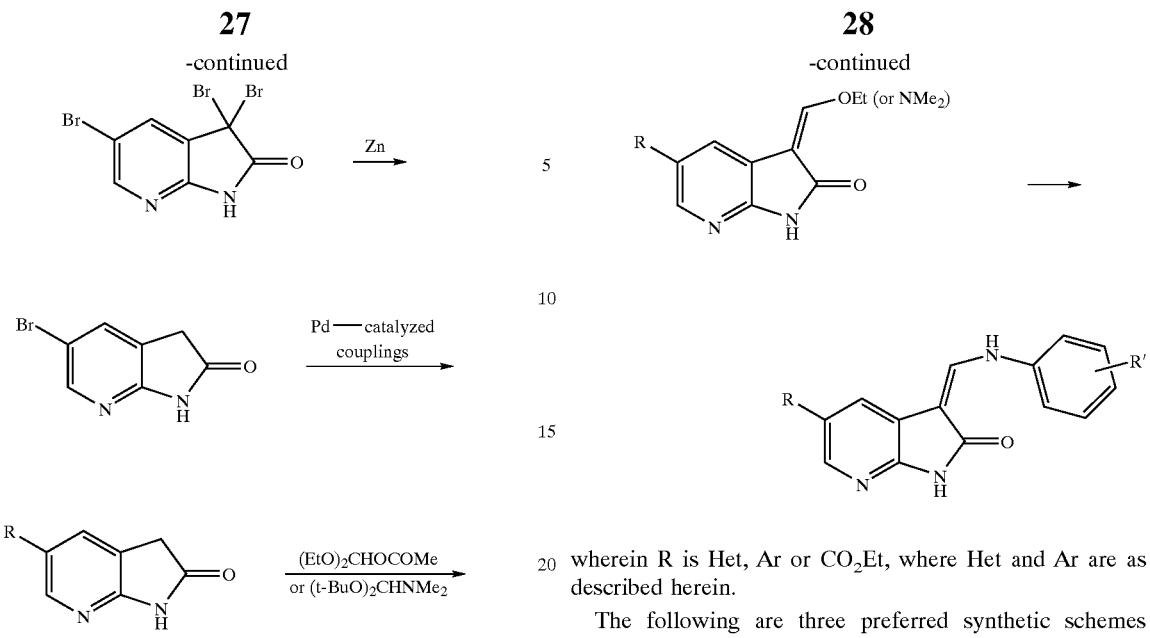
wherein R is Het, Ar or $CO_2Et$, where Het and Ar are as described herein.
The following are three preferred synthetic schemes according to the present invention:
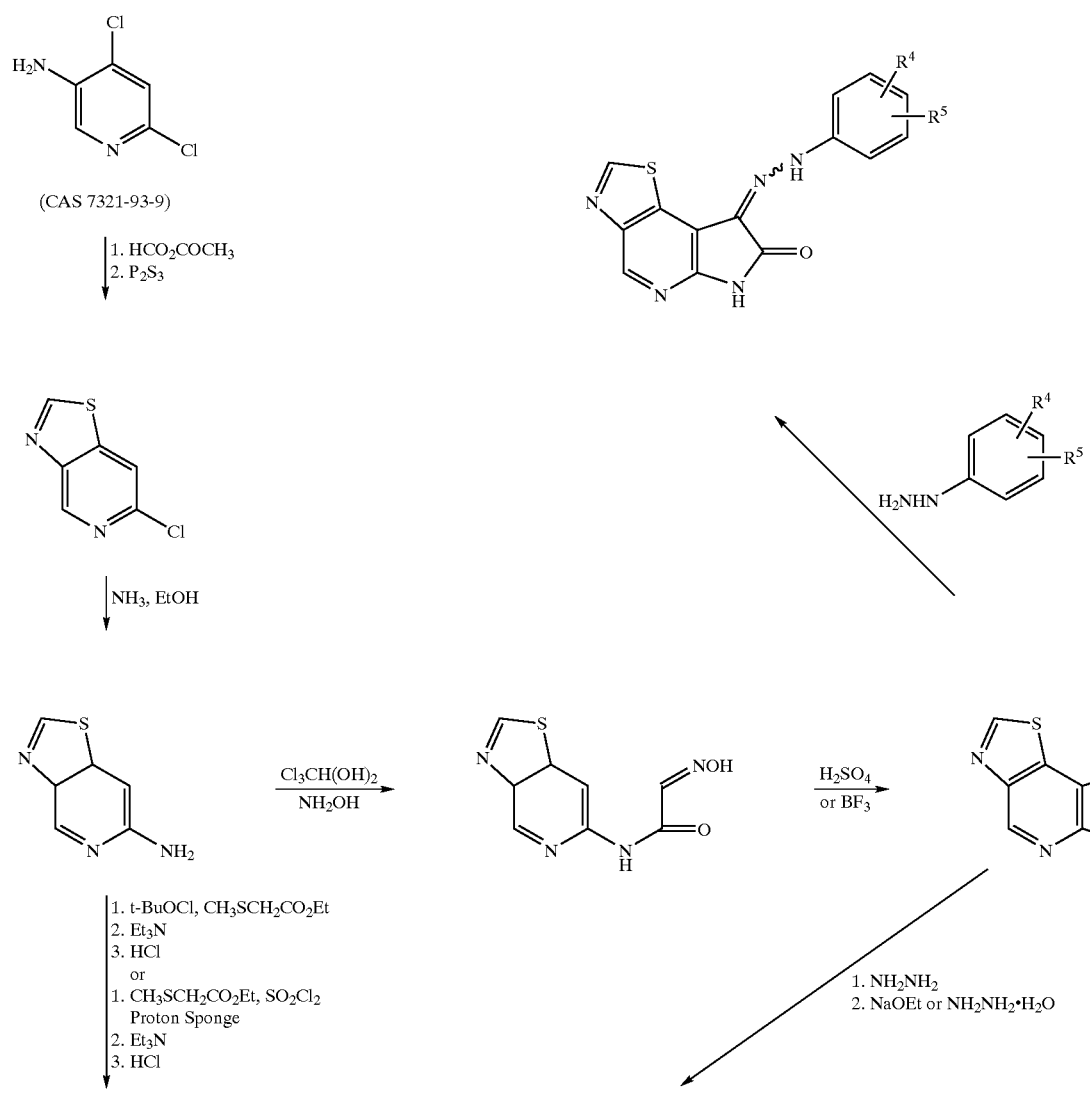

-continued
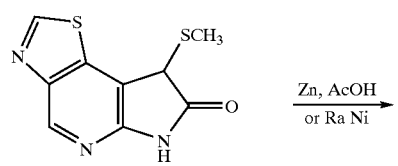 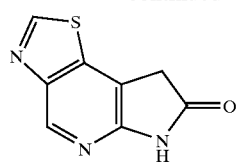 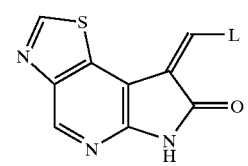
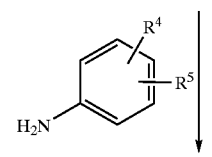
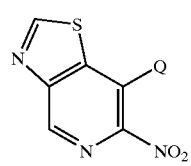 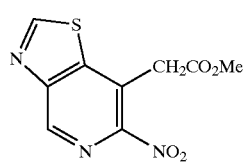 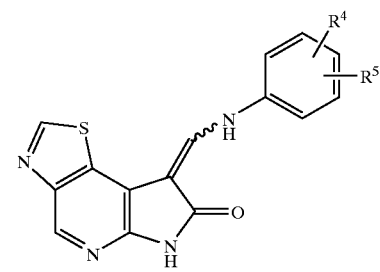
Q = Cl, Br, or F
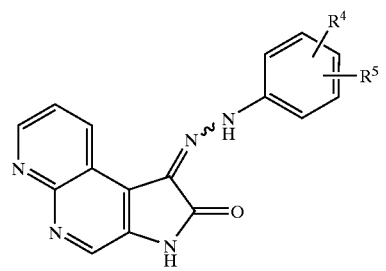
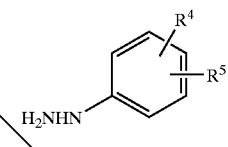
(CAS 5912-36-7)
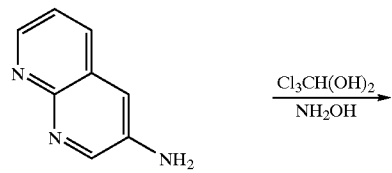 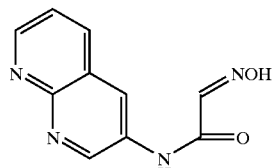 
1. t-BuOCl, CH₃SCH₂CO₂Et
2. Et₃N
3. HCl
   or
1. CH₃SCH₂CO₂Et, SO₂Cl₂
   Proton Sponge
2. Et₃N
3. HCl
1. NH₂NH₂
2. NaOEt or NH₂NH₂·H₂O

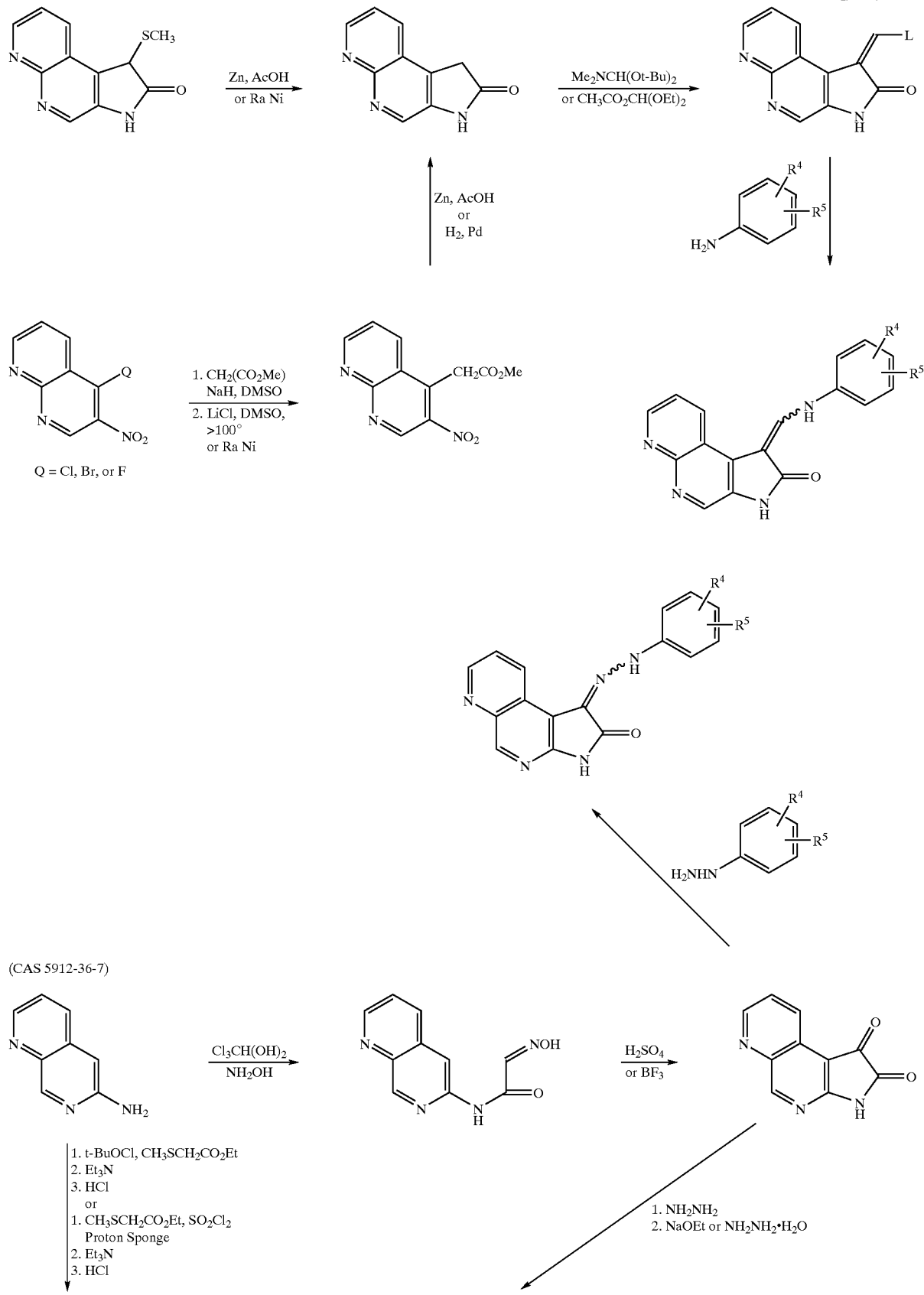

-continued

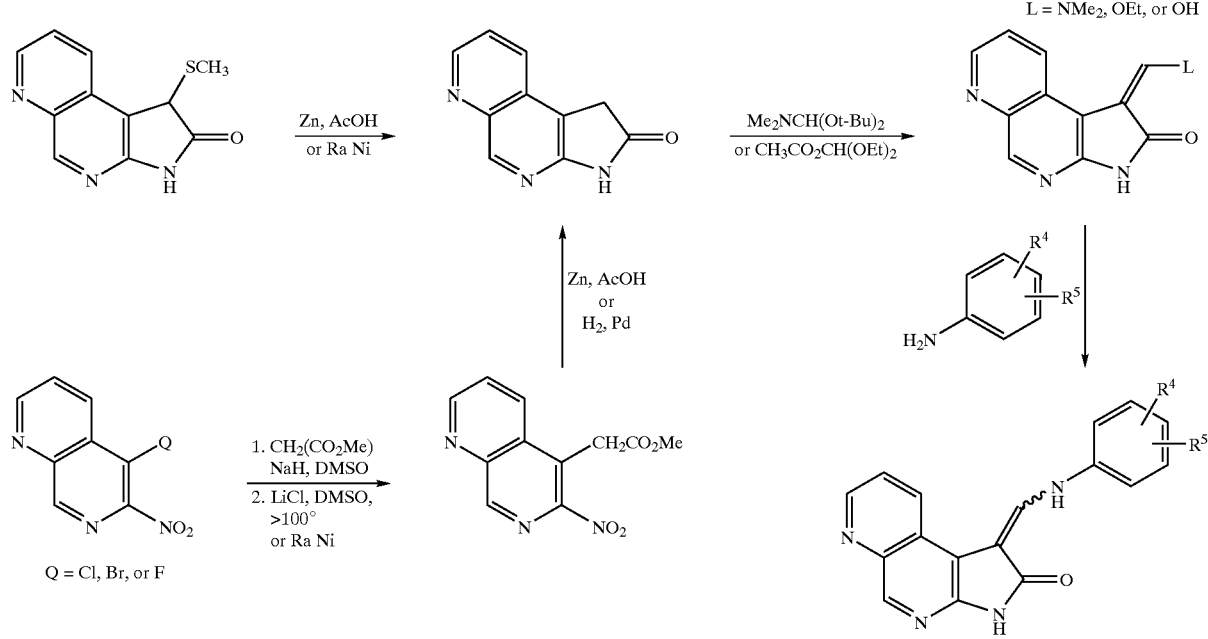

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

| | |
|---|---|
| g = | grams |
| mg = | milligrams |
| L = | liters |
| mL = | milliliters |
| M = | molar |
| N = | normal |
| mM = | millimolar |
| i.v. = | intravenous |
| p.o. = | per oral |
| s.c. = | subcutaneous |
| Hz = | hertz |
| mol = | moles |
| mmol = | millimoles |
| mbar = | millibar |
| psi = | pounds per square inch |
| rt = | room temperature |
| min = | minutes |
| h = | hours |
| mp = | melting point |
| TLC = | thin layer chromatography |
| $R_f$ = | relative TLC mobility |
| MS = | mass spectrometry |
| NMR = | nuclear magnetic resonance spectroscopy |
| APCI = | atmospheric pressure chemical ionization |
| ESI = | electrospray ionization |
| m/z = | mass to charge ratio |
| $t_r$ = | retention time |
| Pd/C = | palladium on activated carbon |

-continued

| | |
|---|---|
| ether = | diethyl ether |
| MeOH = | methanol |
| EtOAc = | ethyl acetate |
| TEA = | triethylamine |
| DIEA = | diisopropylethylamine |
| THF = | tetrahydrofuran |
| DMF = | N,N-dimethylformamide |
| DMSO = | dimethylsulfoxide |
| DDQ = | 2,3-dichloro-5,6-dicyano-1,4-benzoquinone |
| LAH = | lithium aluminum hydride |
| TFA = | trifluoroacetic acid |
| LDA = | lithium diisopropylamide |
| THP = | tetrahydropyranyl |
| NMM = | N-methylmorpholine, 4-methylmorpholine |
| HMPA = | hexamethylphosphoric triamide |
| DMPU = | 1,3-dimethypropylene urea |
| d = | days |
| ppm = | parts per million |
| kD = | kiloDalton |
| LPS = | lipopolysaccharide |
| PMA = | phorbol myristate acetate |
| SPA = | scintillation proximity assay |
| EDTA = | ethylenediamine tetraacetic acid |
| FBS = | fetal bovine serum |
| PBS = | phosphate buffered saline solution |
| BrdU = | bromodeoxyuridine |
| BSA = | bovine serum albumin |
| FCS = | fetal calf serum |
| DMEM = | Dulbecco's modified Eagle's medium |
| pfu = | plaque forming units |
| MOI = | multiplicity of infection |

Reagents are commercially available or are prepared according to procedures in the literature. The physical data given for the compounds exemplified is consistent with the assigned structure of those compounds.

$^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

A Micromass Platform II mass spectrometer equipped with an electrospray ion source was used to acquire low resolution LC-MS data for the samples that were prepared in library format. The system software runs on a PC computer with the Microsoft operating system, and consists of Masslynx v3.1 and Openlynx v3.1 software packages. The mass spectrometer inlet system was comprised of a Hewlett Packard 1100 HPLC Chromatograph, a Gilson 215 autosampler, and a Hewlett Packard 1100 photo-diode array detector. A Supelco ABZ+5 cm column was used to provide separations prior to electrospray ionization. The HPLC was programmed as follows:

| Time Flow Rate | % A | % B |
| --- | --- | --- |
| 0.0 min 0.6 ml/min | 85 | 15 |
| 3.0 min 0.6 ml/min | 25 | 75 |
| 4.0 min 0.6 ml/min | 0 | 100 |
| 5.0 min 0.6 ml/min | 0 | 100 |

The data were processed automatically using standard peak detection parameters provided by the Openlynx software.

Micromass LCT bench-top mass spectrometer equipped with an electrospray ionization source was used to obtain accurate mass data for the samples that were prepared in library format. The LCT utilizes two hexapole RF lenses to transfer ions from the source to an orthogonal acceleration time-of-flight (TOF) analyser. The ions emerging from the analyser are detected using a dual microchannel plate detector and ion counting system. The system software runs on a PC computer with the Microsoft operating system, and consists of Masslynx v3.2 and Openlynx v3.2 software packages. The mass spectrometer inlet system is comprised of a Waters Alliance 2690 Separations Module, Waters 2700 autosampler, Waters 996 photo-diode array detector and Valco column switching device. A mobile phase flow rate of 1 ml/min exits the Alliance 2690 and is reduced to a mass spectrometer flow rate of 20 ul/min using an Acurate flow splitter. A lock mass solution at a flow rate of 4 ul/min is added to the spectrometer flow via a Harvard syringe pump and a tee piece placed immediately before the electrospray probe. The instrument resolution was determined by acquiring a spectrum and measuring the full peak width t half peak height (FWHH). The instrument was tuned to provide a resolution of 4600 to 5000 (FWHH). The instrument was calibrated using the ions of polyethylene glycol (PEG) as reference standards. The lock mass used [3,5-Dil-Tyr, Ala, N-Me-Phe, Gly-01] Enkephalin (MH+C26H34I2N5O6=766.0599) at a concentration of 5 ng/ul.

EXAMPLE 1

4-{[(2-Oxo-1,2-dihydro-3H-pyrrolo[3,2-c]pyridin-3-ylidene)-methyl]amino}benzenesulfonamide a) 3-Dimethylamino-methylene-1,5-diazainden-2-one 3-Bromo4-nitropyridine-1-oxide was prepared according to the procedure of Daisley and Hanbali (Org. Prep. Proced. Int. 1983, 15, 280) and converted to 1,5-diazaindene via the method of Sakamoto et. al. (Heterocycles 1992, 34, 2379). 1,5-Diazaindene was subsequently converted to 1,5-diazainden-2-one hydrobromide via the procedure outlined by Robinson and Donahue (J. Org. Chem. 1991, 56, 4805) and reaction of this with N,N-dimethylformamide-di-t-butyl acetal in DMF gave 3-dimethylamino-methylene-1,5-diazainden-2-one (as described for the reparation of 3-dimethylamino-methylene-1,6-diazainden-2-one): $^1$H NMR DMSO-d$_6$): δ 3.35 (s, 6H), 7.13 (d, J=6.1 Hz, 1H), 8.09 (s, 1H), 8.20 (d, J=6.1 Hz, 1H), 8.57 (s, 1H), 11.50 (s, 1H); $C_{10}H_{11}N_3O$: APES+MS: m/z 190 (M+H).

b) 4-{[(2-Oxo-1,2-dihydro-3H-pyrrolo[3,2-c]pyridin-3-ylidene)methyl]amino}-benzenesulfonamide (mixture of E and Z isomers)

3-Dimethylamino-methylene-1,5-diazainden-2(3H)-one was reacted with sulfanilamide in ethanol with hydrochloric acid to give the title compound (by the method described for Example 2, section f) as a 15:4 mixture of Z:E isomers. $^1$H NMR (DMSO-d$_6$, peak areas normalized using the overlapping peak at δ 8.45 as 1H): δ 7.37 (m, 3H), 7.72 (d, J=8.8 Hz, 2H), 7.86 (d, J=8.8 Hz, 2H), 8.18 E (d, J=14.2 Hz, 0.21H), 8.45 (m, 1H), 8.96 Z (s, 0.79H), 9.14 Z (d, J=13.5 Hz, 0.79H), 9.48 E (s, 0.21H), 10.7 E (m, 0.21H), 10.98 Z (d, J=13.5 Hz, 0.79H), 11.88 E (s, 0.21H), 12.11 Z (s, 0.79H), 14.7 (br s, 1H); $C_{14}H_{12}N_4O_3S$: APES+MS m/z 317 (M+H).

EXAMPLE 2

4-{[(2-Oxo-1,2-dihydro-3H-pyrrolo[2,3-c]pyridin-3ylidene)methyl]amino}benzenesulfonamide a) 3-Nitro-4-pyridinyl-propanedioic acid diethyl ester To a suspension of 3.05 g of 60% sodium hydride (76.0 mmol) in toluene (50 mL) in a 250 mL RB flask was added 12.2 g of diethyl malonate (76.0 mmol) dropwise. The reaction mixture was stirred for 30 min under nitrogen, and a solution of 10.8 g of 4-chloro-3-nitropyridine (prepared according to the procedure of Houston et al. J. Med. Chem. 1985, 28, 467) in toluene (50 mL) was added dropwise and the resulting mixture refluxed for 4 h. The reaction mixture was concentrate, and the residue was partitioned between 100 mL each of dilute hydrochloric acid and diethyl ether. The aqueous phase was extracted twice with 100 mL of ether, and the combined ether phases were dried over magnesium sulfate and concentrated to give a dark oil. This was chromatographed on silica gel eluting With a hexane-30% hexane/EtOAc gradient to give 3.5 g of the title compound as a colorless oil which crystallized on standing. $^1$H NMR (DMSO-d$_6$): δ 1.15 (t, J=7.1 Hz, 6H), 4.16 (q, J=7.1 Hz, 4H), 5.55 (s, 1H), 7.59 (d, J=5.1 Hz, 1H), 8.89 (d, J=5.1 Hz, 1H), 9.24 (s, 1H); $C_{12}H_{14}N_2O_6$: APES–MS m/z 281 (M–H).

b) 3-Nitro4-pyridineacetic acid ethyl ester

To a 100 ml RB flask was added 1.5 g (5.3 mmol) of 3-nitro4-pyridinyl-propanedioic acid diethyl ester, 0.450 g (10.6 mmol) of lithium chloride, 0.095 g (5.3 mmol) of water and 35 mL of DMSO. The solution was heated at 100° C. for 4 h. The cooled reaction mixture was diluted with ethyl acetate (50 mL) and washed successively with water (50 mL) and brine (50 mL). The organic phase was dried over sodium sulfate, filtered and concentrated, and the residue was chromatographed on silica gel eluting with a hexane-10% EtOAc/hexane gradient to give 0.76 g of the title compound as a yellow solid. $^1$H NMR (DMSO-d$_6$): δ 1.14 (t, J=7.1 Hz, 3H), 4.06 (q, J=7.1 Hz, 2H), 4.12 (s, 2H), 7.63 (d, J=4.9 Hz, 1H), 8.82 (d, J=4.9 Hz, 1H), 9.21 (s, 1H); $C_9H_{10}N_2O_4$: APES+MS m/z 211 (M+H).

c) 3-Amino-4-pyridineacetic acid ethyl ester

To a 250-ml Parr flask was added 0.30 g (1.4 mmol) of 3-nitro-4-pyridineacetic acid ethyl ester, 50 mg of 10% palladium on charcoal and 100 mL of ethanol. The mixture was subjected to hydrogenation using a Parr hydrogenator at 40 PSI for 15 min. The mixture was filtered through celite, and the filtrate was concentrated to give an oil which crystallised under a high vacuum to afford 0.282 g of the title compound as a yellow solid. $^1$H NMR (DMSO-$d_6$): δ 1.15 (t, J=7.2 Hz, 3H), 3.52 (s, 2H), 4.05 (q, J=7.2 Hz, 2H), 5.11 (s, 2H), 6.89 (d, J=4.8 Hz, 1H), 7.67 (d, J=4.8 Hz, 1H), 7.92 (s, 1H).

d) 1,6-diazainden-2(3H)-one hydrochloride

To a 50-ml round-bottom flask was added 0.36 g (2.0 mmol) of 3-amino-4-pyridineacetic acid ethyl ester, 15 mL of ether and 10 mL of 10% hydrochloric acid. The resulting biphasic solution was stirred for 16 h at room temperature. The two phases were separated, and the ether phase was washed with 5 mL of water. The combined aqueous phases were evaporated to dryness to yield 0.285 g of the title compound as a brown solid. $^1$H NMR (DMSO-$d_6$): δ 5.93 (s, 1H), 7.59 (d, J=5.6 Hz, 1H), 8.02 (s, 1H), 8.49 (d, J=5.6 Hz, 1H), 12.54 (s, 1H), 14.0 (bs, 1H); $C_8H_6N_2O$: APCI+MS: m/z 135 (M+H).

e) 3-Dimethylamino-methylene-1,6-diazainden-2(3H)-one

To a suspension of 0.080 g (0.47 mmol) of 1,6-diazainden-2(3H)-one in 10 mL of DMF was added 1.2 g (6.0 mmol) of N,N-dimethylformamide-di-t-butyl acetal. The mixture was stirred at ambient temperature for 2 h, and a dark oil deposited. The DMF was removed under high vacuum, and the residue was passed through a silica gel pad, eluting with ethyl acetate:methanol (1:1). The yellow fractions were pooled, and removal of solvent in vacuo left a brown solid (0.12 g): $^1$H NMR (DMSO-$d_6$): δ 3.3 (s, 6H), 7.35 (d, J=5.0, 1H), 7.80 (bs, 1H), 7.91 (s, 1H), 7.95 (d, J=5.0, 1H), 10.32 (bs, 1H); $C_{10}H_{11}N_3O$: APES+MS: m/z 190 (M+H).

f) 4-{[(2-Oxo-1,2-dihydro-3H-pyrrolo[2,3-c]pyridin-3-ylidene)methyl]amino}-benzenesulfonamide To a 25-ml round-bottom flask was added 0.12 g (0.47 mmol) of 3-dimethylaminomethylene-1,6-diazainden-2(3H)-one, 0.081 g (0.47 mmol) of sulfanilamide, 10 ml of ethanol and two drops of concentrated hydrochloric acid. The reaction mixture was refluxed using an oil bath with stirring for 3 h, then cooled and filtered. The collected solid was dissolved in a minimum volume of hot methanol. Upon cooling, a dark material deposited. The methanol solution was decanted and diluted to twice its volume with ethyl acetate. A light brown solid deposited after standing for 48 h. The solid was isolated by filtration, dried, and redissolved in hot methanol (30 mL). The solution was concentrated to 20 mL and diluted with an equal volume of ethyl acetate. On cooling, a tan solid formed. The solid was isolated by filtration and washed with methanol/ethyl acetate to give 25 mg (17%) of the title compound. $^1$H NMR (DMSO-$d_6$): δ 7.42 (s, 2H), 7.82 (d, J=8.5 Hz, 2H), 7.90 (d, J=8.5 Hz, 2H), 8.28 (s, 1H), 8.11 (d, J=6.0 Hz, 1H), 8.38 (d, J=6.0 Hz, 1H), 9.35 (d, J=13.5 Hz, 1H), 11.53 (s, 1H), 11.60 (d, J=13.5 Hz, 1H), 14.6 (br s, 1H); $C_{14}H_{12}N_4O_3S$: APCI–MS m/z 315 (M–H).

EXAMPLE 3

4-{[(2-Oxo-1,2-dihydro-3H-pyrrolo[2,3-b]pyridin-3-ylidene)methyl]amino}benzenesulfonamide Dimethylformamide di-tert-butyl acetal (180 mg, 0.89 mmol) was added to a solution of 1,2-dihydro-3H-pyrrolo[2,3-b]pyridin-2-one (70 mg, 0.52 mmol) in 0.25 ml DMF, and the reaction mixture was slowly warmed to 100° C. The cooled solution was then diluted with 5 ml of ethanol. Sulfanilamide (172 mg, 1.00 mmol) and methanesulfonic acid (60 mg, 0.63 mmol) were added, and the reaction mixture was stirred at reflux for 2 h. The cooled solution was diluted with 4 ml of water, treated with NaHCO$_3$ (70 mg, 0.83 mmol) and stirred 10 min. The resulting solid was filtered, washed with water and ethanol, and then suspended in boiling methanol and filtered upon cooling.

Inorganics were removed by filtration through a short silica gel column, eluting with DMF. The resulting solution was diluted with an equal volume of ice water, and the suspension was refrigerated overnight. The solid was isolated by filtration and dried to give 36 mg (21%) of the title compound as a yellow solid: $^1$H NMR (400 MHz, DMSO-$d_6$) (4:1 ratio of Z:E isomers): δ (Z) 11.07 (s, 1H), 10.76 (d, J=12.4 Hz, 1H), 8.67 (d, J=12.5 Hz, 1H), 7.92 (d, J=5.1 Hz, 1H), 7.84 (d, J=7.3 Hz, 1H), 7.77 (d, J=8.7 Hz, 2H), 7.55 (d, J=8.6 Hz, 2H), 7.25 (s, 2H), 6.93 (dd, J=7.3, 5.1 Hz, 1H); (E) 10.79 (s, 1H), 9.70 (d, J=13.4 Hz, 1H), 8.23 (d, J=7.3 Hz, 1H). ESI-MS m/z 315 (M–H). Anal. Calcd. for $C_{14}H_{12}N_4O_3S \cdot 0.5H_2O$: C, 51.68; H, 4.03; N, 17.03. Found: C, 51.75; H, 3.95; N, 17.26.

Compounds Prepared Via Solution Phase Library Techniques (Parallel Synthesis)

We now set forth a selected number of synthesis examples that illustrate the solution library techniques that can be used to obtain the compounds of the invention. It is believed that one of ordinary skill in the art will, in view of the synthesis scheme set forth below (Scheme 7), be able to follow this procedure or modify it accordingly without undue experimentation in order to obtain any of the substitutions disclosed above. The following examples are illustrative examples of the solution phase synthesis, not intended to limit the scope of the invention in any way.

Scheme 7.
Preparation of pyrrolopyridinones
via Solution Phase Library Techniques

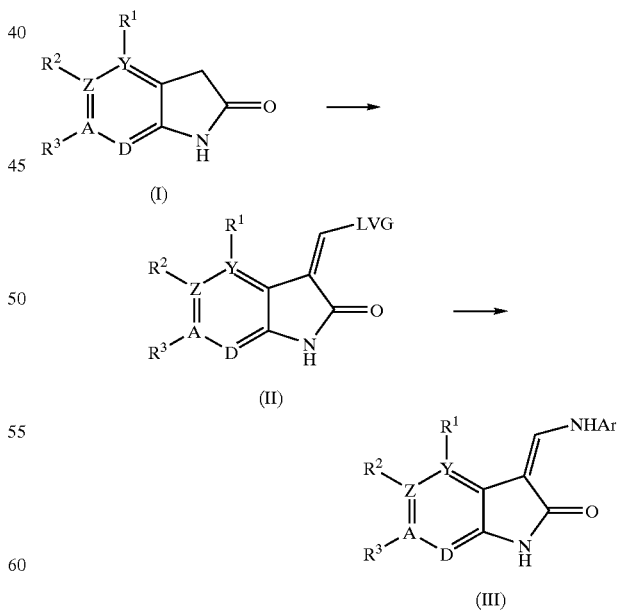

wherein R$^1$, R$^2$, R$^3$, Y, Z, A, D and Ar are as defined hereinabove, and wherein LVG is a leaving group selected from the group including: OCH$_3$, OCH$_2$CH$_3$, OH, N(CH$_3$)$_2$.

Synthesis of Intermediates

5-Bromo-1,3-dihydro-2H-pyrrolo[2,3-b]pyridin-2-one a) 3,3,5-Tribromo-1,3-dihydro-2H-pyrrolo[2,3-b]pyridin-2-one A solution of 3,3-dibromo-1,3-dihydro-2H-pyrrolo[2,3-b]pyridin-2-one (5.0 g, 13.4 mmol) in tert-BuOH (100 mL) and water (100 mL) was stirred at room temperature and bromine (5.5 g, 34.3 mmol) was added dropwise over min. A saturated aqueous solution of sodium bicarbonate (approx. 15 mL) was added dropwise over 30 min to raise the pH of the solution to 6.5. The yellow solid formed was collected by filtration. The filtrate was condensed to approx. 100 mL and extracted with $CHCl_3$ (2×50 mL). The combined organic extracts were dried over anhydrous magnesium sulfate, and the solvent was evaporated under reduced pressure to leave a yellow solid. The solids were combined and dried under vacuum to give 3,3,5-tribromo-1,3-dihydro-2H-pyrrolo[2,3-b]pyridin-2-one as a yellow solid, 6.25 g (98%). $^1$H NMR ($CDCl_3$) δ 9.4 (br s, 1H), 8.28 (d, 1H, J=2 Hz), 7.95 (d, 1H, J=2 Hz).

b) 5-Bromo-1,3-dihydro-2H-pyrrolo[2,3-b]pyridin-2-one

A solution of 3,3,5-tribromo-1,3-dihydro-2H-pyrrolo[2,3-b]pyridin-2-one (5.0 g, 13.4 mmol) in fresh THF (100 mL) was stirred at room temperature, and a saturated aqueous solution of ammonium chloride (100 mL) was added. The flask was placed in a water bath, and activated zinc dust (15.0 g, 230 mmol) was added. The mixture was stirred for 20 min, and the zinc was removed by filtration through a pad of diatomaceous earth. The organic layer was separated, and the aqueous layer was extracted with THF (20 mL). The combined organic layers were washed with saturated brine solution and dried over anhydrous magnesium sulfate. Solvent was removed under reduced pressure. The brown residue was triturated with water (20 mL), and the tan solid was collected by filtration and dried under vacuum to give the title compound as a tan solid, 2.02 g (71%). $^1$H NMR ($d_6$-DMSO) δ 11.13 (s, 1H), 8.15 (s, 1H), 8.76 (s, 1H), 3.57 (s, 2H). MS (AP−ve) 211 (100)(M−H).

5-Phenyl-1,3-dihydro-2H-pyrrolo[2,3-b]pyridin-2-one

To a stirred mixture of 5-bromo-1,3-dihydro-2H-pyrrolo[2,3-b]-pyridin-2-one (213 mg, 1 mmol) and phenylboronic acid (183 mg, 1.5 mmol) in toluene (6 ml) and ethanol (6 ml) were added 1 M sodium carbonate solution (2.5 ml, 2.5 mmol), lithium chloride (127 mg, 3 mmol) and dichlorobis(triphenylphosphine)-palladium(II) (35 mg, 0.05 mmol) under $N_2$ atmosphere. The reaction mixture was heated to reflux at 95° C. for 18 hours. The reaction mixture was diluted with chloroform (50 ml) and washed with brine (20 ml). The aqueous layer was thoroughly extracted with chloroform. The combined organic lay rs wer dried over anhydrous $MgSO_4$, filtered and evaporated under vacuum to give crude product. Trituration of the crude product with diethyl ether yielded 5-phenyl-1,3-dihydro-2H-pyrrolo[2,3-b]pyridin-2-one as a yellow solid (108 mg, 51.4%). $^1$H NMR ($d_6$-DMSO): δ 11.04 (s, 1H), 8.32 (s, 1H), 7.83 (s, 1H), 7.60 (d, 2H, J=7.4 Hz), 7.44 (t, 2H, J=7.4 Hz), 7.32 (t, 1H, J=7.4 Hz), 3.58 (s, 2H). MS (−ve APCI): 210 (48, M$^+$), 209 (100, M−H).

5-(2-Furyl)-1,3-dihydro-2H-pyrrolo[2,3-b]pyridin-2-one

5-Bromo-1,3-dihydro-2H-pyrrolo[2,3-b]pyridin-2-one (0.75 g; 3.52 mmol), 2-tributyltinfuran (1.26 g, 3.52 mmol), tetraethylammonium chloride hydrate (1.94 g, 10.6 mmol) were combined and dissolved in acetonitrile (10 mL) at room temperature under an atmosphere of nitrogen. Bistriphenylphosphine dichloropalladium (II) (0.25 g, 0.35 mmol) was added, and the reaction was warmed to 85° C. for 16 h. The reaction was cooled to room temperature and diluted with aqueous KF (10%, 60 mL). This was stirred for 20 minutes and then diluted with EtOAc (60 mL). The biphasic system was passed through celite, the layers separated, and the volatiles removed in vacuo. The resulting residue was triturated with diethyl ether, and the solids were collected by filtration to afford the title compound as a light yelow solid (0.28 g, 36% yield). $^1$H NMR 300 MHz (DMSO-$d_6$): δ 11.18 (bs, 1H); 8.45 (s, 1H); 7.92 (s, 1H); 7.79 (s, 1H); 6.95 (d, 1H); 6.60 (d, 1H); 3.64 (s, 2H). APCI m/z 201 (M+1).

5-(3-thienyl)-1,3-dihydro-2H-pyrrolo[2,3-b]pyridin-2-one

5-Bromo-1,3-dihydro-2H-pyrrolo[2,3-b]pyridin-2-one (0.20 g, 0.94 mmol), 3-tributyltinthiophene (0.42 g, 1.12 mmol), tetraethylammonium chloride hydrate (0.16 g, 0.94 mmol) were combined and dissolved in acetonitrile (10 mL) at room temperature under nitrogen. Bistriphenylphosphine dichloropalladium (II) (0.033 g, 0.047 mmol) was added, and the reaction was warmed to 85° C. for 20 h. Fresh catalyst (bistriphenylphosphine dichloropalladium (II), 0.033 g, 0.047 mmol) was added to the reaction mixture, and the reaction was stirred at 85° C. for 24 h. The reaction was cooled to room temperature and diluted with water (20 mL) and EtOAc (20 ml). The biphasic system was passed through celite, and the layers were separated. The organic layer was washed with brine (10 mL) and dried over sodium sulfate. The volatiles were removed in vacuo. The resulting residue was triturated with diethyl ether and collected by filtration to provide the title compound (0.16 g, 80% yield). $^1$H NMR 400 MHz (DMSO-$d_6$) δ 11.03 (bs, 1H); 8.43 (s, 1H); 7.92 (s, 1H); 7.84 (s, 1H); 7.60 (m, 1H); 7.53 (d, 1H); 3.58 (s, 2H).

Ethyl 2-oxo-2,3-dihydro-1H-pyrrolo[2,3-b]pyridine-5-carboxylate

To a mixture of 5-bromo-1,3-dihydro-2H-pyrrolo[2,3-b]pyridin-2-one (213 mg, 1 mmol) in dimethylsulfoxide (1 ml) and ethanol (5 ml) in Parr bomb were added triethylamine (0.31 ml, 2.25 mmol), palladium acetate (33.7 mg, 0.15 mmol), and 1,4-(bisdiphenylphosphino)propane (61.9 mg, 0.15 mmol). Carbon monoxide gas (40 atm) was applied and the reaction mixture was heated at 95° C. for 18 hours with vigorous stirring. The reaction mixture was diluted with diethyl ether (50 ml) and washed with water (10 ml). The aqueous layer was thoroughly extracted with diethyl ether. The combined organic layers were dried over anhydrous $MgSO_4$, filtered and evaporated under vacuum to give crude product. Trituration of the crude product with methanol provided the title compound as a tan solid (53 mg, 26%). $^1$H NMR ($d_6$-DMSO): δ 11.39 (s, 1H), 8.62 (s, 1H), 7.95 (s, 1H), 4.27 (q, 2H, J=7 Hz), 3.59 (s, 2H), 1.28 (t, 3H, J=7 Hz). MS (−ve APCI): 205 (4, M−H).

1,3-Dihydro-2H-pyrrolo[2,3-b]pyridin-2-one a) 3,3-dibromo-1,3-dihydro-2H-pyrrolo[2,3-b]pyridin-2-one A solution of pyrrolo[2,3-b]pyridine (4.0 g, 34 mmol) in tert-BuOH (200 mL) was stirred at room temperature and pyridinium perbromide (32.5 g, 0.1 mol) was added in portions over 30 min, and the reaction mixture was stirred for 3 h. Pyridinium perbromide (10.8 g, 33 mmol) was added, and the mixture was stirred for a further 2 h. The tert-BuOH was evaporated under reduced pressure, and the residue was partitioned between water (300 mL) and EtOAc (300 mL). The organic layer was separated, and the aqueous layer was extracted with EtOAc. The combined organic layers were washed with water (2×50 mL) and brine. The organic layer was dried over anhydrous $MgSO_4$ and filtered, and the solvent was evaporated. Trituration of the residue with $CH_2Cl_2$ gave a white solid which was collected by filtration and dried under vacuum to provide 8.35 g of the title compound. $^1$H NMR (d$_6$-DMSO) δ 11.99 (s, 1H), 8.21 (dd, 1H, J=5.1, 1.5 Hz), 8.00 (dd, 1H, J=7.5, 1.5 Hz), 7.17 (dd, 1H, J=7.5, 5.1 Hz). MS (+ve ES) 293 (28), (M+H) 147 (100).

b) 1,3-Dihydro-2H-pyrrolo[2,3-b]pyridin-2-one

A solution of 3,3-dibromo-1,3-dihydro-2H-pyrrolo[2,3-b]pyridin-2-one (2.0 g, 7.2 mmol) in THF (50 mL) was stirred at room temperature, and a saturated aqueous solution of NH$_4$Cl was added. Activated zinc powder was added, and the reaction mixture was stirred for 2 h. The zinc was removed by filtration through a pad of diatomaceous earth, and the organic layer was separated. The aqueous layer was extracted with THF (10 mL), and the combined organic layers were dried over anhydrous MgSO$_4$, filtered and evaporated. The residue was slurried in 10:1 CHCl$_3$:MeOH (15 mL) and filtered through a pad of silica gel, and the filtrate was evaporated. The residue was triturated with water, and the solid was collected by filtration and dried under vacuum to give the title compound, 0.668 g (70%). $^1$H NMR (d$_6$-DMSO) δ 10.94 (s, 1H), 8.02 (d, 1H, J=5.2 Hz), 7.52 (d, 1H, J=6.8 Hz), 6.90 (dd, 1H, J=6.8, 5.2 Hz), 3.53 (s, 2H). MS (AP–ve) 133 (100)(M–H)

1,3-Dihydro-2H-pyrrolo[3,2-b]pyridin-2-one a) Diethyl (3-nitropyridin-2-yl)-malonate Sodium hydride (60% dispersion in oil, 5.57 g, 0.14 mol) was carefully washed with hexanes under nitrogen before the addition of DMSO (115 mL). Diethyl malonate (22.3 g, 0.14 mol) was added dropwise over 20 min, and the mixture was stirred for an additional 30 min at room temperature. 2-Chloro-3-nitropyridine (10 g, 0.06 mol) was added to the reaction, and the reaction was placed in a pre-heated oil bath set to 100° C. for 15 min. The reaction was cooled to room temperature and poured into aqueous ammonium chloride (saturated solution, 150 mL). The aqueous solution was extracted with EtOAc:hexanes (1:1) four times (200 mL each), and the organic layers were combined. The organics were concentrated to afford a solid that was recrystallized from a minimal amount of EtOAc:hexanes (1:1) to provide the title compound (12.5 g, 70% yield). APCI MS m/z 281 (M–H).

b) Ethyl 2-(3-nitro-pyridin-2-yl)-acetate

Diethyl (3-nitropyridin-2-yl)-malonate (12.5 g, 0.044 mol) was dissolved in DMSO (150 mL), and water (0.79 mL, 0.044 mol) and lithium chloride (4.65 g, 0.11 mol) were added at room temperature under nitrogen. The reaction was warmed to 100° C. for 12 h, and more lithium chloride (1 g) was added to the reaction. The reaction was heated for another 5 hours and cooled to room temperature. Brine (150 mL) was added, and the reaction mixture was extracted with EtOAc (3×275 mL). The extracts were combined, dried over sodium sulfate and concentrated in vacuo. The resulting residue was triturated with diethyl ether and collected by filtration to yield the title compound (8.6 g, 92% yield). $^1$H NMR 400 MHz (DMSO-d$_6$): δ 8.83 (m, 1H); 8.53 (m, 1H); 7.65 (m, 1H); 4.23 (s, 2H); 4.07 (m, 2H); 1.16 (m, 3H).

c) Ethyl 2-(3-amino-pyridin-2-yl)-acetate

Under an atmosphere of nitrogen, Pd/C (10%, 1.36 g) was added to a round bottom flask. Ethyl 2-(3-nitro-pyridin-2-yl)-acetate (8.6 g, 0.41 mol) was dissolved in ethanol (200 mL) and added to the reaction vessel. The reaction was placed under an atmosphere of hydrogen and stirred at room temperature for 30 min. The reaction was filtered through celite, and the filtrate was concentrated in vacuo to afford the title compound as a tan solid (6.94 g, 94% yield).

d) 1,3-Dihydro-2H-pyrrolo[3,2-b]pyridin-2-one

Ethyl 2-(3-amino-pyridin-2-yl)-acetate (6.94 g, 0.038 mol) was dissolved in diethyl ether (100 mL) at room temperature. Hydrochloric acid (2M, 35 mL) was added, and the reaction was stirred for 30 minutes. The volatiles were removed to afford a brown solid that was recrystallized from ethanol and diethyl ether to provide the title compound (4.0 g, 62% yield). $^1$H NMR 400 MHz (DMSO-d$_6$): δ 12.35 (s, 1H); 8.12 (m, 1H); 7.90 (m, 1H); 7.14 (m, 1H); 5.75 (s, 2H). Electrospray MS m/z 135 (M+H).

6-Chloro-1,3-dihydro-2H-pyrrolo[2,3-b]pyridin-2-one a) 3,3-Dibromo-6-chloro-1,3-dihydro-2H-pyrrolo[2,3-b]pyridin-2-one To a stirred solution of 1.32 g (8.7 mmol) of 6-chloro-1H-pyrrolo[2,3-b]-pyridine (Minakata et al., Synthesis 1992, 661–663) in tert-butanol (80 mL) was added 9.9 g (28 mmol) of 90% pyridine hydrobromide perbromide, resulting in immediate formation of a thick yellow precipitate. The reaction was concentrated, and the crude residue was chromatographed on silica gel, eluting with a hexane to 90% hexane/10% EtOAc gradient, to give 2.36 g of the title compound as a white solid [$^1$H NMR (CDCl$_3$): δ 7.16 (d, J=8.0 Hz, 1H), 7.81 (d, J=8.0 Hz, 1H) 9.0 (bs, 1H)] containing about 30% of 3,3,5-tribromo-6-chloro-1,3-dihydro-2H-pyrrolo[2,3-b]pyridin-2-one as an inseparable impurity [$^1$H NMR δ 8.05 (s, 1H), 9.0 (bs, 1H)].

b) 6-Chloro-1,3-dihydro-2H-pyrrolo[2,3-b]pyridin-2-one

A solution of 2.36 g (7.26 mmol) of the mixture of 3,3-dibromo-6-chloro-1,3-dihydro-2H-pyrrolo[2,3-b]pyridin-2-one and 3,3,5-tribromo-6-chloro-1,3-dihydro-2H-pyrrolo[2,3-b]pyridin-2-one in THF (70 mL) and saturated ammonium chloride solution (70 mL) was treated with, 6 g (92 mmol) of powdered zinc. The mixture was stirred for 2 h, and another 6 g (92 mmol) portion of zinc was added. Stirring was continued another 2 h. The zinc was filtered off and washed with ether. The ether phase was separated, and the aqueous phase was extracted twice with a 1:1 mixture of THF/ether. The combined organic extracts were dried over magnesium sulfate, filtered and concentrated. The crude residue was loaded onto 7.5 g of silica gel and chromatographed on silica gel, eluting with a 90% hexane/10% ethyl acetate to 66% hexane/33% ethyl acetate gradient to give 0.647 g of the title compound. $^1$H NMR (DMSO-d$_6$): δ 3.57 (s, 2H), 7.04 (d, J=7.6 Hz, 1H), 7.61 (d, J=7.6 Hz, 1H), 11.2 (bs, 1H).

Synthesis of Monomers

Ethyl 3-[(Z)-ethoxymthyliden]-2-oxo-1,2-dihydro-3H-pyrrolo[2,3-b]pyridine-5-carboxylate (Procedure A)

Ethyl 2-oxo-2,3-dihydro-1H-pyrrolo[2,3-b]pyridine-5-carboxylate (0.040 g, 0.19 mmol) and diethoxymethyl acetate (0.16 mL, 0.97 mmol) were combined and dissolved in acetic acid (1 mL). The reaction was warmed to 110° C. and stirred at this temperature for 1 h. The reaction was cooled to room temperature, and diethyl ether was added to precipitate the title compound as a beige solid that was collected by filtration (35 mg, 69% yield). $^1$H NMR 400 MHz (DMSO-d$_6$): δ 11.30 (s, 1H); 8.58 (s, 1H); 8.05 (s, 1H); 7.93 (s, 1H); 4.44 (m, 2H); 4.28 (m, 2H); 1.35 (m, 3H); 1.28 (m, 3H).

3-[Ethoxymethylidene]-5-phenyl-1H-pyrrolo[2,3-b]pyridin-2-one

This compound was synthesized from 5-phenyl-1,3-dihydro-2H-pyrrolo[2,3-b]pyridin-2-one and diethoxymethyl acetate according to Procedure A. $^1$H NMR 400 MHz (DMSO-d$_6$): δ 10.93 (s, 1H); 8.24 (s, 1H); 7.86–7.82 (m, 2H); 7.62–7.56 (m, 2H); 7.44 (m, 2H); 7.34 (m, 1H); 4.40 (m, 2H); 1.35 (m, 3H).

3-[Ethoxymethylidene]-5-(2-furyl)-1H-pyrrolo[2,3-b]pyridin-2-one

This compound was synthesized from 5-(2-furyl)-1,3-dihydro-2H-pyrrolo[2,3-b]pyridin-2-one and diethoxymethyl acetate according to Procedure A. $^1$H NMR 400 MHz (DMSO-d$_6$): δ 10.96 (s, 1H); 8.36 (s, 1H); 7.87–7.84 (m, 2H); 7.72 (s, 1H); 6.87 (d, 1H); 6.56 (m, 1H); 4.42 (m, 2H); 1.36 (m, 3H).

3-[Ethoxymethylidene]-5-(3-thienyl)-1H-pyrrolo[2,3-b]pyridin-2-one

This compound was synthesized from 5-(3-thienyl)-1H-pyrrolo[2,3-b]pyridin-2-one and diethoxymethyl acetate according to Procedure A. $^1$H NMR 400 MHz (DMSO-d$_6$): δ 10.89 (s, 1H); 8.33 (s, 1H); 7.88 (s, 1H); 7.84 (s, 1H); 7.79 (s, 1H); 7.62 (m, 1H); 7.49 (d, 1H); 4.40 (m, 2H); 1.36 (m, 3H).

5-Bromo-3-[ethoxymethylidene]-1H-pyrrolo[2,3-b]pyridin-2-one

This compound was synthesized from 5-bromo-1H-pyrrolo[2,3-b]pyridin-2-one and and diethoxymethyl acetate according to Procedure A. $^1$H NMR 400 MHz (DMSO-d$_6$): δ 11.02 (s, 1H); 8.07 (s, 1H); 7.88 (s, 1H); 7.71 (s, 1H); 4.40 (m, 2H); 1.34 (m, 3H).

6-Chloro-3-[ethoxymethylidene]-1H-pyrrolo[2,3-b]pyridin-2-one

This compound was synthesized from 6-chloro-1H-pyrrolo[2,3-b]pyridin-2-one and diethoxymethyl acetate according to Procedure A. $^1$H NMR 400 MHz (DMSO-d$_6$): δ 11.06 (s, 1H); 7.84 (s, 1H); 7.63 (d, 1H); 6.98 (d, 1H); 4.39 (m, 2H); 1.32 (m, 3H).

3-[(Dimethylamino)methylidene]-1H-pyrrolo[2,3-b]pyridin-2-one

This compound was prepared in situ (during library synthesis) from 1,3-dihydro-2H-pyrrolo[2,3-b]pyridin-2-one and dimethylformamide di-t-butylacetal in DMF.

3-[(Dimethylamino)methylidene]-1H-pyrrolo[3,2-b]pyridin-2-one

This monomer was generated in situ (during library synthesis) from 1,3-dihydro-2H-pyrrolo[3,2-b]pyridin-2-one and dimethylformamide di-t-butylacetal in DMF.

Solution Phas Library Synthesis

The compounds described here were prepared as part of a larger library of related compounds using the following procedure. Stock solutions (0.037M in ethanol) were prepared for each set of pyrrolopyridinone monomers. For the aniline set (4-aminobenzenesulfonamide, 1H-indazol-6-amine, and 6-quinolinamine), a slight excess of stock solution was prepared.

3-[(Dimethylamino)methylidene]-1H-pyrrolo[2,3-b]pyridin-2-one and 3-[(dimethylamino)methylidene]-1H-pyrrolo[3,2-b]pyridin-2-one were generated in situ by preparing stock solutions of the corresponding pyrrolopyridinone. For example, 20.1 mg of 1,3-dihydro-2H-pyrrolo[3,2-b]pyridinone was dissolved in 4.0 mL of ethanol. Both of the pyrrolopyridinones were transferred (0.20 ml/well) to a 96-well dry heating block (vwrBRAND Dry Block Heater, cat #13259-066). The ethanol was evaporated off at 50° C. until it was clear that there was no solvent remaining. DMF (0.20 mL) was added followed by the addition of dimethylformamide di-t-butylacetal (0.003 mL), and this remained at room temperature for 1 h.

The ethoxymethylidenepyrrolopyridinones (0.20 mL/well) were transferred to wells in the dry block heater. The aniline set (0.20 mL/well) was transferred to the appropriate wells such that each pyrrolopyridinone was reacted with each aniline. The plates were heated to 70° C. for 4 h, and then the reaction was cooled to 40° C. and heating was continued for another 16 h. Ethanol was added as necessary to keep a constant reaction volume in the wells.

Upon completion of the reaction, methanol (1.0 mL) was added to each well. Using a multi-pipettor, the contents of the reaction wells were transferred to the appropriate wells of a 96-well (Beckmann) plate. The volatiles were removed using a nitrogen flow to substantially reduce the volume of solvent, followed by placing the plat s in a vacuum drying oven at 70° C. under 15 mm Hg of pressure. All of the wells were analysed by LC-MS.

EXAMPLE 3

3-[(1H-Indazol-6-ylamino)methylidene]-1H-pyrrolo[3,2-b]pyridin-2-one

High resolution masspec: calc. for $C_{15}H_{11}N_5O$, 278.1042 (M+H); found, 278.1036.

EXAMPLE 4

3-[(6-Quinolinylamino)methylidene]-1,3-dihydro-2H-pyrrolo[3,2-b]pyridin-2-one

High resolution masspec: calc. for $C_{17}H_{12}N_4O$, 289.1089 (M+H); found, 289.1085.

EXAMPLE 5

4-{[(2-Oxo-1,2-dihydro-3H-pyrrolo[2,3-b]pyridin-3-ylidene)methyl]amino}benzenesulfonamide Low resolution mass spec: 317 (M+H).

EXAMPLE 6

3-[(1H-Indazol6-ylamino)methylidene]-1H-pyrrolo[2,3-b]pyridin-2-one

High resolution masspec: calc. for $C_{15}H_{11}N_5O$, 278.1042 (M+H); found, 278.1033.

EXAMPLE 7

3-[(6-Quinolinylamino)methylidene]-1,3-dihydro-2H-pyrrolo[2,3-b]pyridin-2-one

High resolution masspec: calc. for $C_{17}H_{12}N_4O$, 289.1089 (M+H); found, 289.1079.

EXAMPLE 8

4-{[(2-Oxo-5-phenyl-1,2-dihydro-3H-pyrrolo[2,3-b]pyridin-3-ylidene)methyl]amino}benzenesulfonamide High resolution masspec: calc. for $C_{20}H_{16}N_4O_3S$, 393.1021 (M+H); found, 393.1003.

EXAMPLE 9

3-[(1H-Indazol-6-ylamino)methylidene]-5-phenyl-1H-pyrrolo[2,3-b]pyridin-2-one

High resolution masspec: calc. for $C_{21}H_{15}N_5O$, 354.1355 (M+H), found, 354.1336.

EXAMPLE 10

5-Phenyl-3-[(6-quinolinylamino)methylidene]-1,3-dihydro-2H-pyrrolo[2,3-b]pyridin-2-one High resolution masspec: calc. for $C_{23}H_{16}N_4O$, 365.1402 (M+H); found, 365.1396.

EXAMPLE 11

4-({[5-(2-Furyl)-2-oxo-1,2-dihydro-3H-pyrrolo[2,3-b]pyridin-3-ylidene]methyl}amino)benzenesulfonamide High resolution masspec: calc. for $C_{18}H_{14}N_4O_4S$, 383.0814 (M+H); found, 383.0800.

EXAMPLE 12

5-(2-Furyl)-3-[(1H-indazol-6-ylamino)methylidene]-1H-pyrrolo[2,3-b]pyridin-2-one Low resolution masspec: 344 (M+H).

EXAMPLE 13
5-(2-Furyl)-3-[(6-quinolinylamino)methylidene]-1,3-dihydro-2H-pyrrolo[2,3-b]pyridin-2-one High resolution masspec: calc. for $C_{21}H_{14}N_4O_2$, 355.1195 (M+H); found, 355.1182.

EXAMPLE 14
4-({[2-Oxo-5-(3-thienyl)-1,2-dihydro-3H-pyrrolo[2,3-b]pyridin-3-ylidene]methyl}amino)benzenesulfonamide Low resolution masspec: 399 (M+H).

EXAMPLE 15
3-[(1H-indazol-6-ylamino)methylidine]-543-thienyl)-1,3-dihydro-2H-pyrrolo[2,3-b]pyridin-1-one High resolution masspec: calc. for $C_{19}H_{13}N_5OS$, 360.0919 (M+H); found, 360.0903.

EXAMPLE 16
3-[(6-Quinolinylamino)methylidene]-5-(3-thienyl)-1,3-dihydro-2H-pyrrolo[2,3-b]pyridin-2one High resolution masspec: calc. for $C_{21}H_{14}N_4OS$, 371.0966 (M+H); found, 371.0956.

EXAMPLE 17
4-{[(5-Bromo-2-oxo-1,2-dihydro-3H-pyrrolo[2,3-b]pyridin-3-ylidene)methyl]amino}benzenesulfonamide High resolution masspec: calc. for $C_{14}H_{11}BrN_4O_3S$, 394.9813 (M+H); found, 394.9792.

EXAMPLE 18
5-Bromo-3-[(1H-indazol-6-ylamino)methylidene]-1,3-dihydro-2H-pyrrolo[2,3-b]pyridin-2-one High resolution masspec: calc. for $C_{15}H_{10}BrN_5O$, 356.0146 (M+H); found, 356.0135.

EXAMPLE 19
5-Bromo-3-[(6quinolinylamino)methylidene]-1,3-dihydro-2H-pyrrolo[2,3-b]pyridin-2-one High resolution masspec: calc. for $C_{17}H_{11}BrN_4O$, 367.0194 (M+H); found, 367.0177.

EXAMPLE 20
4-{[(6-Chloro-2-oxo-1,2-dihydro-3H-pyrrolo[2,3-b]pyridin-3-ylidene)methyl]amino}benzenesulfonamide High resolution masspec: calc. for $C_{14}H_{11}ClN_4O_3S$, 351.0318 (M+H); found, 351.0315.

EXAMPLE 21
6-Chloro-3-[(1H-indazol-6-ylamino)methylidene]-1,3-dihydro-2H-pyrrolo[2,3-b]pyridin-2-one High resolution masspec: calc. for $C_{15}H_{10}ClN_5O$, 312.0652 (M+H); found, 312.0628.

EXAMPLE 22
6-Chloro-3-[(6-quinolinylamino)methylidene]-1,3-dihydro-2H-pyrrolo[2,3-b]pyridin-2-one High resolution masspec: calc. for $C_{17}H_{11}ClN_4O$, 323.0699 (M+H); found, 323.0697.

EXAMPLE 23
Ethyl 3-{[4-(aminosulfonyl)anilino]methylidene}-2-oxo-1,2-dihydro-3H-pyrrolo[2,3-b]pyridine-5-carboxylate High resolution masspec: calc. for $C_{17}H_{16}N_4O_5S$, 389.0919 (M+H); found, 389.0914.

EXAMPLE 24
Ethyl 3-[(1H-indazol-6-ylamino)methylidene]-2-oxo-1,2-dihydro-3H-pyrrolo[2,3-b]pyridine-5-carboxylate High resolution masspec: calc. for $C_{18}H_{15}N_5O_3$, 350.1253 (M+H); found, 350.1241.

EXAMPLE 25
Ethyl 2-oxo-3-[(6-quinolinylamino)methylidene]-2,3-dihydro-1H-pyrrolo[2,3-b]pyridine-5-carboxylate High resolution masspec: calc. for $C_{20}H_{16}N_4O_3$, 361.1300 (M+H); found, 361.1299.

Pharmaceutical Formulation and Doses

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 100 mg/kg of body weight per day, and particularly 1 to 10 mg/kg of body weight per day. Oral dosage units will generally be administered in the range of from 1 to about 250 mg and more preferably from about 25 to 250 mg. The daily dosage for a 70 kg mammal will generally be in the range of about 70 mg to 7 grams of a compound of formula I or II.

While the dosage to be administered is based on the usual conditions such as the physical condition of the patient, age, body weight, past medical history, route of administrations, severity of the conditions and the like, it is generally preferred for oral administration to administer to a human. In some cases, a lower dose is sufficient and, in some cases, a higher dose or more doses may be necessary. Topical application similarly may be once or more than one per day depending upon th usual m dical considerations. Advantageously, compounds of the present invention may be administered in a single daily dose, or the total daily dosage may be administered in divided doses of two, three or four times daily. The compounds of the invention can be prepared in a range of concentrations for topical use of 0.1 to 5 mg/ml of suitable solvent. A preferred volume for application to the scalp is 2 to 20 ml, resulting in an effective dosage delivered to the patient of 0.2 to 100 mg. For treatment of chemotherapy-induced alopecia, administration 1 to 2 times prior to chemotherapy administration would be preferred,,with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a is suitably flavored aqueous solution, while elixirs are prepared through the use of a non-toxic alcoholic vehicle. Suspensions can be formulated by dispersing the compound in a non-toxic vehicle. Solubilizers and emulsifiers. such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers Useful in achieving controlled release of a drug, for example, polylactic acid, polepsilon caprolactone, polyhydroxy butyric acid, polyorthoesters, polyacetals, polydihydropyrans; polycyanoacrylates and cross-linked or amphipathic block copolymers of hydrogels.

The present invention includes pharmaceutical compositions containing 0.01 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ster as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents, to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or. insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

Biological Data

The compounds of the present invention have valuable pharmacologic properties. Different compounds from this, class are particularly effective at inhibiting the CDK1 and CDK2 enzymes at concentrations which range from 0.01 to 3 $\mu$M and additionally show specificity relative to other kinases. Substrate phosphorylation assays were carried out as follows:

CDK2

Cyclin dependent protein kinase assays utilized the peptides Biotin-aminohexyl-AAKAKKTPKKAKK and Biotin-aminohexyl-ARRPMSPKKKA-NH$_2$ as phosphoryl group acceptors. CDK2 was expressed utilizing a baculovirus expression system and was partially purified to comprise 20–80% of total protein, with no detectable competing reactions present. Typically, assays were performed by incubating enzyme (0.2–10 nM), with and without inhibitor, one of the two peptide substrates (1–10 nM), [$\gamma$-$^{32}$P]ATP (1–20 nM), and 10–20 mM Mg$^{2+}$ for periods of time generally within the range 10–120 min. Reactions were terminated with 0.2–2 volumes of either 20% acetic acid or 50–100 mM EDTA buffered to pH 7 (substrate consumption <20%). The buffer employed in enzyme assays was either 30 mM HEPES 7.4 containing 0.15 M NaCl and 5% DMSO, the buffer 50 mM MOPS 7.0 containing 0.15 M NaCl and 5% DMSO, or the buffer 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham; reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=V$_{max}$*(1−([I]/(K+[I])))+nsb, or pIC50s were determined by a fit to the equation CPM=nsb+(V$_{max}$−nsb)/(1+(x/10$^x$-pIC50)), where nsb are the background counts.

VEGFR-2

The peptide substrate used in the VEGFR-2 assay was biotin-aminohexyl-EEEEYFELVAKKKK-NH$_2$. The kinase domain of the enzyme was purified to homogeneity from a baculovirus expression system. The enzyme was preactivated on ice for 15 min in the presence of 100 $\mu$M ATP and 20 mM MgCl$_2$, and stored at −80° C. until needed for assay. The activated enzyme was diluted to 0.4 nM into a 60 $\mu$l reaction containing 100 mM HEPES, pH 7.5, 5 $\mu$M ATP, 10 mM MgCl$_2$, 5 $\mu$M peptide, 0.1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by the addition of EDTA to 60 mM in 210 $\mu$l. The quenched samples (190 $\mu$l) were transferred to a neutravidin-coated plate (Pierce) and incubated at room temperature for 40 min to allow biotinylated peptide to bind to the neutravidin. The unbound components of the reaction were removed by washing with a plate washer, then 200 $\mu$l HRP-PY20 anti-phosphotyrosine antibody conjugate was added to each well. After incubation for 40 min, the plate was washed to remove any unbound anitbody. A HRP substrate, K-blue (Neogen) was added and the reaction was quenched with Red Stop (Neogen) after 20 min. The absorbance of the wells was read at A$_{650}$ in a plate reader. IC$_{50}$ values were obtained by fitting raw data to A$_{650}$=V$_{MAX}$*(1−[I]/IC$_{50}$+[I]))+b, where b is background.

c-fms c-fms protein kinase assays utilized the peptide substrate, biotin-EAIYMPFAKKK-NH$_2$ as the phosphoryl group acceptor. The c-fms intracellular domain was expressed from a baculovirus expression system, as an amino-terminal GST fusion protein, and purified to homogeneity using Glutathione agarose from Sigma Chemical Co. Maximum activation of the enzyme was achieved by preactivation at room temperature for 120 min in the presence of 100 $\mu$M ATP and 15 mM MgCl$_2$, This enzyme stock was diluted to 150 nM prior to using in the assay. Typically assays were performed in white, opaque, 96-well plates in a 45 ul assay volume including 15 ul 6% DMSO, with or without compounds, 15 ul of the preactivated, diluted enzyme, and 15 ul of a substrate mixture. Reactions contained 50 mM HEPES, pH 7.5, 1.7 $\mu$M ATP, 15 mM MgCl$_2$, 3 $\mu$M peptide, 2.5 mM DTT, 50 mM NaCl and 0.15 uCi/assay [□□$^{32}$P] ATP. The controls were reactions in the presence (negative controls) or absence (positive controls) of 50 mM EDTA. Reactions were allowed to proceed for 90 min at room temperature. The reaction products were quantified using Scintillation Proximity technolgy. The reactions were quenched by the addition of 200 ul of a solution containing 0.3 mg streptavidin SPA beads from Amersham, 50 mM EDTA, 0.1% TX-100, 50 uM ATP, in PBS, pH7.2 (phosphate buffered solution). Plates were sealed and counted in a Packard Topcount scintillation counter. IC50 values were obtained by fitting raw data to the equation y=Vmax*(1−(x/(k+x))).

The results shown in Table 3 summarise representative data: Table 3 illustrates the inhibitory activity of compounds of the present invention against three different kinases (CDK2, c-fms,and VEGFR2).

TABLE 3

Kinase inhibition data of representative compounds

| Example | CDK2 | C-FMS | VEGFR2 |
|---|---|---|---|
| 1 | +++ | | + |
| 2 | +++ | | |
| 3 | | | + |
| 4 | | | + |
| 5 | ++ | | + |
| 6 | | + | ++ |

TABLE 3-continued

Kinase inhibition data of representative compounds

| Example | CDK2 | C-FMS | VEGFR2 |
|---|---|---|---|
| 7  |     |     | +   |
| 8  | +   |     |     |
| 9  |     | +   |     |
| 10 |     | +   |     |
| 11 | +++ | ++  | +   |
| 12 | +   | +   | ++  |
| 13 |     | +   | +   |
| 14 | ++  | ++  | ++  |
| 15 | ++  | +   | +   |
| 16 |     | ++  | +   |
| 17 | +++ | +   | ++  |
| 18 | +++ | +   | ++  |
| 19 | +++ | +   | ++  |
| 20 | ++  |     | ++  |
| 21 | ++  | +   | ++  |
| 22 |     | +   | +   |
| 23 | +++ | +   | ++  |
| 24 | +++ | +   | +++ |
| 25 | ++  |     | ++  |

Key (IC$_{50}$, μM)
0.01–0.1: +++
0.1–1.0: ++
1.0–10: +

Utility of Invention

Inhibitors of members of the CDK family of kinases find utility as agents in the treatment of a wide variety of disorders which have a proliferative component or which involve regulation of cyclin dependent kinase function. These include cancers, restenosis, psoriasis, and actinic keratosis.

The present invention demonstrates methodologies by which the onset of cell death in normal proliferating cells induced by chemotherapeutic drugs may be prevented by the prior treatment with inhibitors of cyclin dependent kinases. This may be useful to decrease the severity of chemotherapy-induced side effects due to killing of normal cells. These side effects may include, but are not limited to alopecia, mucocitis (nausea and vomiting, diahrea, oral lesions), neutropenia and thrombocytopenia. Inhibitors of cyclin dependent kinases CDK2 and CDK4 prevent the progression of normal cells into both S-phase (DNA synthesis) or M-phase (mitosis), reducing their susceptibility to incur damage by certain chemotherapeutic drugs which act in those phases of the cell cycle. When the compounds of the present invention are used in conjunction with chemotherapeutic agents, they may reduce the severity of chemotherapy-induced side effects.

The compounds of the present invention may also be used in combination with radiation treatment to show similar protection of normal cells from the effects of radiation and may be used as radiosensitizers to increase the tumour killing by radiation therapy.

The compounds of the present invention which are inhibitory for CDK4 or CDK6. activity will selectively inhibit cell cycle progression in cells which retain a functional retinoblastoma protein. Thus, it will be expected that inhibition of CDK4 will systemically protect normal dividing cells, including the GI and oral mucosa, hematopoietic cells and cells in the hair follicle, but be unable to protect tumour cells with loss of RB function, either by deletion or mutation. This implies that compounds that inhibit CDK4 will be useful as systemically administered cytoprotectant drugs in patients with tumours which have lost Rb, with no protective effect on the tumour itself. Such compounds could be expected to allow for increased dosing frequency and dose escalation of the cytotoxic regimens in these patients, improving the outcome of the patient.

The compounds of the present invention may also be used for the treament of other conditions mentioned in connection with modulators of CDK activity. In particular for the treatment of diseases that respond to inhibition of CDK activity, including protection of cells from infection by other viruses and treatment of Alzheimers. Furthermore, these compounds will have utility in the specific inhibition of non-human CDK activities, such as the *Aspergillus fumigatus* cdc2 homologue and will therefore be useful in the treatment of fungal or other eukaryotic infections.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invenion. It is intended, therefore, that the invention be limited only by the scope of the claims that follow and that such claims be interpreted as broadly as is reasonable.

The application of which this description and claim(s) forms part may be used as a basis for priority in respect of any subsequent application. The claims of such subsequent application may be directed to any feature or combination of features described herein. They may take the form of product, formulation, process or use claims and may include, by way of example and without limitation, one or more of the following claim(s):

What is claimed is:

1. A compound of the formula:

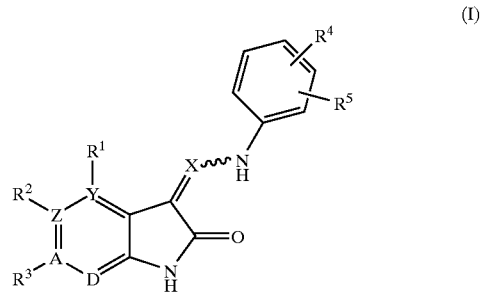

(I)

wherein:
X is CH;
Y is C;
Z is C;
A is C;
D is N;
R$^1$ is selected from the group consisting of: hydrogen, C$_{1-12}$ aliphatic, thiol, hydroxy, hydroxy-C$_{1-12}$ aliphatic, Aryl, Aryl-C$_{1-12}$ aliphatic, R$^6$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide and nitro, where $R^6$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl and $C_{1-12}$ aliphatic-aminosulfonyl, where $R^6$ Aryl and Het are as defined below;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy and halogen, where Aryl and Het are as defined below;

$R^4$ is selected from the group consisting of: sulfonic acid, $C_{1-12}$ aliphatic-sulfonyl, sulfonyl-$C_{1-12}$ aliphatic-sulfonyl, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)$1-3-Arylamino, $(R^8)$1-3-Arylsulfonyl, $(R^8)$1-3-Aryl-aminosulfonyl, $(R^8)$1-3-Aryl-sulfonylamino, Het-amino, Het-sulfonyl, Het-aminosulfonyl, aminoiminoamino and aminoiminoaminosulfonyl, where $R^7$, $R^8$, Aryl and Het are as defined below;

$R^5$ is hydrogen or $R^4$ and $R^5$ are optionally joined to form a fused ring selected from the group as defined for Het below, and said fused ring is optionally substituted by one or more substituents selected from the group consisting of: $C_{1-12}$ aliphatic, oxo and dioxo;

$R^6$ is selected from the group consisting of: $C_{1-12}$ aliphatic, hydroxy, $C_{1-12}$ alkoxy and halogen;

$R^7$ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxy-alkoxyalkoxyaliphatic and hydroxyl, where Het and Aryl are as defined below;

$R^8$ is selected from the group consisting of: hydrogen, nitro, cyano, $C_{1-12}$ alkoxy, halo, carbonyl-$C_{1-12}$ alkoxy and halo-$C_{1-12}$ aliphatic;

Aryl is selected from the group consisting of: phenyl, naphthyl, phenanthryl and anthracenyl;

Cyc is selected from the group consisting of: cyclopropyl, cyolobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolldine, oxazine, oxadiazine, piperazine, piperadine, pyran, pyrazine, pyrazole, pyridine, pyrimidine, pyrrole, pyrrolidine, quinoline, tetrahydrofuran, tetrazine, thidiazine, thiadiazole, thiatriazole, thiazine, thiazole, thiomorpholine, thiophene, thiopyran, triazine and triazole;

and the pharmaceutically acceptable salts, solvates, polymorphs, and/or prodrugs thereof.

2. The compound of claim 1, where $R^1$ is hydrogen, halogen, amide, nitro, lower alkyl, hydroxy, hydroxyalkyl, pyrimidineloweralkyl, loweralkoxycarbonyl, cyclic loweralkyl, hydroxyphenylloweralkyl, phenoxy, alkoxy and pyrazole.

3. The compound of claim 1, where $R^1$ is hydrogen or methyl.

4. The compound of claim 1, where $R^1$ is hydrogen.

5. The compound of claim 1, where $R^2$ is hydrogen, halogen, sulfate, amine, quaternary amine, amide, ester, phenyl, alkoxy, aminosulfonyl, lower alkyl sulfonyl, furanyl lower alkyl amide, pyridinyl lower alkyl amide, alkoxy-substituted phenyl lower alkyl amide, morpholino lower alkyl amid, imidazolyl lower alkyl amide, hydroxy lower alkyl amide, alkoxy lower alkyl amide, lower alkyl amide, lower alkyl sulfonamide, lower alkyl hydroxy substituted amino, nitro, halogen-substituted phenoxycarbonyl and triazole and oxazole rings.

6. The compound of claim 1, where $R^2$ is selected from the group consisting of hydrogen, phenyl, 2-furanyl, 3-thiophenyl, bromo, and carbethoxy.

7. The compound of claim 1, where $R^3$ is selected from the group consisting of hydrogen, lower alkyl, hydroxyl, lower alkyl, halogen, phenoxy and alkoxy.

8. The compound of claim 1, where $R^3$ is hydrogen or chloro.

9. The compound of claim 1 where $R^3$ is hydrogen.

10. The compound of claim 1 where $R^4$ is selected from the group consisting of sulfonylamino, sulfonylaminoamino, lower alkyl sulfonylamino, lower alkylsulfonyl lower alkyl, alkoxysulfonylamino, phenylcarbonylsulfonylamino, phenoxysulfonyl, hydroxy lower alkylsulfonylamino, hydroxy lower alkylsulfonylamino lower alkyl, alkyl, phenylsulfonylamino (optionally substituted by halogen-substituted lower alkyl), aminoiminosulfonylamino, alkylsulfonylaminoalkyl, pyridinyl lower alkyl sulfonylamino, benzamideazolesulfonylamino, pyridylsulfonylamino, pyrimidinylsulfonylamino, thiadiazolylsulfonylamino (optionally substituted by lower alkyl), thiazolesulfonylamino, hydroxyalkoxyalkylsulfonylamino and 4'-$SO_2NH[(CH_2)_2O]_4CH_3$.

11. The compound of claim 1 where $R^4$ is selected from the group consisting of 2-pyridine sulfonylamino, 4-pyridine sulfonylamino, hydroxy n-butyl sulfonylamino, methylsulfonylaminomethylene, sulfonyldimethylamino, fused 1,2-pyrazole and sulfonylamino.

12. The compound of claim 1 where $R^4$ is sulfonylamino or fused 1,2-pyrazole.

13. The compound of claim 1 where $R^4$ is fused with $R^5$ to form a fused ring selected from the group consisting of imidazole, triazole, cyclic sulfonylamino and thiaphene, where said fused ring is optionally disubstituted on the sulfur heteroatom by oxo.

14. The compound of claim 1 where $R^5$ is hydrogen.

15. The compound of claim 1 where $R^6$ is selected from the group consisting of: hydrogen, $C_{1-6}$ aliphatic, hydroxy, $C_{1-6}$ alkoxy and halogen.

16. The compound of claim 1 where $R^6$ is selected from the group consisting of: hydroxy, $C_{1-6}$ alkoxy and halogen.

17. The compound of claim 1 where $R^8$ is hydrogen or halo $C_{1-6}$ aliphatic.

18. The compound of claim 1 where $R^8$ is trifluoromethyl.

19. A composition comprising one or more compounds in E, Z or E and Z form, selected from the group consisting of:

4-{[(2-Oxo-1,2-dihydro-3H-pyrrolo[2,3-b]pyridin-3-ylidene)methyl]amino}benzenesulfonamide;

3-[(1H-Indazol-6-ylamino)methylidene]-1H-pyrrolo[2,3-b]pyridin-2-one;

3-[(6-Quinolinylamino)methylidene]-1,3-dihydro-2H-pyrrolo[2,3-b]pyridin-2-one;

3-[(6-Quinolinylamino)methylidene]-1,3-dihydro-2H-pyrrolo[3,2-b]pyridin-2-one;

4-{[(2-Oxo-5-phenyl-1,2-dihydro-3H-pyrrolo[2,3-b]pyridin-3-ylidene)methyl]amino}benzenesulfonamide;

3-[(1H-Indazol-6-ylamino)methylidene]-5-phenyl-1H-pyrrolo[2,3-b]pyridin-2-one;

5-Phenyl-3-[(6-quinolinylamino)methylidene]-1,3-dihydro-2H-pyrrolo[2,3-b]pyridin-2-one;

4-({[5-(2-Furyl)-2-oxo-1,2-dihydro-3H-pyrrolo[2,3-b]pyridin-3-ylidene]methyl}amino)benzenesulfonamide;

5-(2-Furyl)-3-[(1H-indazol-6-ylamino)methylidene]-1H-pyrrolo[2,3-b]pyridin-2-one;

5-(2-Furyl)-3-[(6-quinolinylamino)methylidene]-1,3-dihydro-2H-pyrrolo[2,3-b]pyridin-2-one;

4-({[2-Oxo-5-(3-thienyl)-1,2-dihydro-3H-pyrrolo[2,3-b]pyridin-3-ylidene]methyl}amino)benzenesulfonamide;

3-[(1H-indazol-6-ylamino)methylidene]-5-(3-thienyl)-1,3-dihydro-2H-pyrrolo[2,3-b]pyridin-2-one;

3-[(6-Quinolinylamino)methylidene]-5-(3-thienyl)-1,3-dihydro-2H-pyrrolo[2,3-b]pyridin-2-one;

4-{[(5-Bromo-2-oxo-1,2-dihydro-3H-pyrrolo[2,3-b]pyridin-3-ylidene)methyl]amino}benzenesulfonamide;

5-Bromo-3-[(1H-indazol-6-ylamino)methylidene]-1,3-dihydro-2H-pyrrolo[2,3-b]pyridin-2-one;

5-Bromo-3-[(6-quinolinylamino)methylidene]-1,3-dihydro-2H-pyrrolo[2,3-b]pyridin-2-one;

4-{[(6-Chloro-2-oxo-1,2-dihydro-3H-pyrrolo[2,3-b]pyridin-3-ylidene)methyl]amino}benzenesulfonamide;

6-Chloro-3-[(1H-indazol-6-ylamino)methylidene]-1,3-dihydro-2H-pyrrolo[2,3-b]pyridin-2-one;

6-Chloro-3-[(6-quinolinylamino)methylidene]-1,3-dihydro-2H-pyrrolo[2,3-b]pyridin-2-one;

Ethyl 3-{[4-(aminosulfonyl)anilino]methylidene}-2-oxo-1,2-dihydro-3H-pyrrolo[2,3-b]pyridine-5-carboxylate;

Ethyl 3-[(1H-indazol-6-ylamino)methylidene]-2-oxo-1,2-dihydro-3H-pyrrolo[2,3-b]pyridine-5-carboxylate; and Ethyl 2-oxo-3-[(6-quinolinylamino)methylidene]-2,3-dihydro-1H-pyrrolo[2,3-b]pyridine-5-carboxylate.

20. A compound as claimed in claim 1 in the form of a substantially pure E geometric isomer.

21. A compound as claimed in claim 1 in the form of a substantially pure Z geometric isomer.

22. A compound as claimed in claim 1 in the form of a mixture of E geometric isomer and Z geometric isomer.

23. A pharmaceutical composition, comprising a compound as claimed in claim 1, and one or more pharmaceutically acceptable carriers, excipients, or diluents.

* * * * *